(12) United States Patent
Terasaki et al.

(10) Patent No.: US 9,504,144 B2
(45) Date of Patent: Nov. 22, 2016

(54) POWER MODULE SUBSTRATE, POWER MODULE SUBSTRATE WITH HEAT SINK, POWER MODULE, METHOD OF MANUFACTURING POWER MODULE SUBSTRATE, AND COPPER MEMBER-BONDING PASTE

(71) Applicant: MITSUBISHI MATERIALS CORPORATION, Tokyo (JP)

(72) Inventors: Nobuyuki Terasaki, Saitama (JP); Yoshiyuki Nagatomo, Saitama (JP); (Continued)

(73) Assignee: MITSUBISHI MATERIALS CORPORATION, Tokyo (JP)

( * ) Notice: Subject to any disclaimer, the term of this patent is extended or adjusted under 35 U.S.C. 154(b) by 83 days.

(21) Appl. No.: 14/374,092

(22) PCT Filed: Feb. 1, 2013

(86) PCT No.: PCT/JP2013/052347
§ 371 (c)(1),
(2) Date: Jul. 23, 2014

(87) PCT Pub. No.: WO2013/115359
PCT Pub. Date: Aug. 8, 2013

(65) Prior Publication Data
US 2015/0208496 A1   Jul. 23, 2015

(30) Foreign Application Priority Data

Feb. 1, 2012  (JP) .................................. 2012-020171
Feb. 1, 2012  (JP) .................................. 2012-020172
(Continued)

(51) Int. Cl.
*B23K 31/02* (2006.01)
*H05K 1/02* (2006.01)
(Continued)

(52) U.S. Cl.
CPC ........... *H05K 1/0271* (2013.01); *B23K 1/0016* (2013.01); *B23K 35/025* (2013.01); *B23K 35/30* (2013.01);
(Continued)

(58) Field of Classification Search
None
See application file for complete search history.

(56) References Cited

U.S. PATENT DOCUMENTS 5,330,098 A     7/1994  Mizuhara
5,354,415 A *  10/1994  Fushii ..................... H05K 3/06
                                                                216/108
(Continued)

FOREIGN PATENT DOCUMENTS

EP    0153618 A2    9/1985
EP    0798779 A1   10/1997
(Continued)

OTHER PUBLICATIONS

Appeal Decision mailed Jun. 30, 2015, issued for the Japanese patent application No. 2012-267298 and a partial translation thereof.
(Continued)

*Primary Examiner* — Kiley Stoner
(74) *Attorney, Agent, or Firm* — Locke Lord LLP

(57) ABSTRACT

This power module substrate includes a copper plate that is formed of copper or a copper alloy and is laminated on a surface of a ceramic substrate 11; a nitride layer 31 that is formed on the surface of the ceramic substrate 11 between the copper plate and the ceramic substrate 11; and an Ag—Cu eutectic structure layer 32 having a thickness of 15 μm or less that is formed between the nitride layer and the copper plate.

8 Claims, 12 Drawing Sheets

US 9,504,144 B2
Page 2

(72) Inventors: Kimihito Nishikawa, Gotenba (JP);
Yoshirou Kuromitsu, Saitama (JP)

(30) Foreign Application Priority Data

Dec. 6, 2012 (JP) ................................. 2012-267298
Dec. 6, 2012 (JP) ................................. 2012-267299

(51) Int. Cl.
| | |
|---|---|
| *B23K 35/02* | (2006.01) |
| *B23K 35/30* | (2006.01) |
| *B23K 35/32* | (2006.01) |
| *C22C 5/06* | (2006.01) |
| *C22C 14/00* | (2006.01) |
| *C22C 16/00* | (2006.01) |
| *C22C 21/00* | (2006.01) |
| *C22C 27/00* | (2006.01) |
| *C22C 27/02* | (2006.01) |
| *C22C 28/00* | (2006.01) |
| *C22F 1/08* | (2006.01) |
| *H01L 23/373* | (2006.01) |
| *B23K 1/00* | (2006.01) |
| *B23K 35/36* | (2006.01) |
| *H05K 1/03* | (2006.01) |
| *H05K 1/09* | (2006.01) |
| *H05K 1/18* | (2006.01) |
| *H05K 3/38* | (2006.01) |
| *H05K 13/04* | (2006.01) |
| *C04B 37/02* | (2006.01) |

(52) U.S. Cl.
CPC ........... *B23K 35/3006* (2013.01); *B23K 35/32* (2013.01); *B23K 35/36* (2013.01); *C04B 37/026* (2013.01); *C22C 5/06* (2013.01); *C22C 14/00* (2013.01); *C22C 16/00* (2013.01); *C22C 21/00* (2013.01); *C22C 27/00* (2013.01); *C22C 27/02* (2013.01); *C22C 28/00* (2013.01); *C22F 1/08* (2013.01); *H01L 23/3735* (2013.01); *H05K 1/0306* (2013.01); *H05K 1/09* (2013.01); *H05K 1/181* (2013.01); *H05K 3/388* (2013.01); *H05K 13/0465* (2013.01); *B23K 2001/12* (2013.01); *C04B 2237/121* (2013.01); *C04B 2237/125* (2013.01); *C04B 2237/366* (2013.01); *C04B 2237/368* (2013.01); *C04B 2237/402* (2013.01); *C04B 2237/407* (2013.01); *C04B 2237/60* (2013.01); *C04B 2237/706* (2013.01); *C04B 2237/708* (2013.01); *C04B 2237/72* (2013.01); *H01L 2224/32225* (2013.01); *H01L 2924/01322* (2013.01); *H05K 2201/0175* (2013.01); *Y10T 428/12542* (2015.01)

(56) References Cited

U.S. PATENT DOCUMENTS

| | | | | |
|---|---|---|---|---|
| 5,569,958 A | * | 10/1996 | Bloom | .................. C04B 37/006 174/265 |
| 6,221,511 B1 | * | 4/2001 | Sakuraba | ................ B32B 18/00 228/122.1 |
| 6,663,982 B1 | | 12/2003 | Stephens, Jr. et al. | |
| 7,143,929 B2 | * | 12/2006 | Furukawa | ........... H01L 23/3735 174/258 |
| 2009/0101392 A1 | * | 4/2009 | Kaga | ....................... H01L 23/15 174/252 |
| 2012/0015152 A1 | * | 1/2012 | Takahashi | ............. C04B 41/009 428/172 |
| 2014/0126155 A1 | * | 5/2014 | Imamura | ............ B23K 35/3006 361/715 |

FOREIGN PATENT DOCUMENTS

| | | | |
|---|---|---|---|
| EP | 0868961 A1 | | 10/1998 |
| EP | 1965423 A2 | | 9/2008 |
| JP | 60-177634 A | | 9/1985 |
| JP | 64-053795 A | | 3/1989 |
| JP | 64-065859 A | | 3/1989 |
| JP | 04-187574 A | | 7/1992 |
| JP | 05-148053 A | | 6/1993 |
| JP | 05-156303 A | | 6/1993 |
| JP | 06-024854 A | | 2/1994 |
| JP | 06310850 A | * | 11/1994 |
| JP | 06310851 A | * | 11/1994 |
| JP | 07-172944 A | | 7/1995 |
| JP | 09-036540 A | | 2/1997 |
| JP | 09-162325 A | | 6/1997 |
| JP | 10-145039 A | | 5/1998 |
| JP | 11-130555 A | | 5/1999 |
| JP | 11-246289 A | | 9/1999 |
| JP | 2000-031609 A | | 1/2000 |
| JP | 2000-335983 A | | 12/2000 |
| JP | 3171234 B2 | | 5/2001 |
| JP | 3211856 B2 | | 9/2001 |
| JP | 2002-274964 A | | 9/2002 |
| JP | 2003-197824 A | | 7/2003 |
| JP | 2003-285195 A | | 10/2003 |
| JP | 2005-116602 A | | 4/2005 |
| JP | 2005-268821 A | | 9/2005 |
| JP | 2006-120973 A | | 5/2006 |
| JP | 2007-035353 A | | 2/2007 |
| JP | 2008-034860 A | | 2/2008 |
| JP | 2010-114469 A | | 5/2010 |
| JP | 2011-091184 A | | 5/2011 |
| WO | WO-98/54761 A1 | | 12/1998 |

OTHER PUBLICATIONS

International Search Report mailed Mar. 19, 2013, issued for PCT/JP2013/052347.
Office Action mailed Nov. 12, 2013, issued for the Japanese patent application No. 2012-267298 and English translation thereof.
Office Action mailed Nov. 12, 2013, issued for the Japanese patent application No. 2012-267299 and English translation thereof.
Office Action mailed Aug. 25, 2015, issued for the Japanese patent application No. 2014-143522 and English translation thereof.
Search Report dated Jan. 5, 2016, issued for the European patent application No. 13742826.4.
Office Action mailed Feb. 9, 2016, issued for the Japanese patent application No. 2015-127751 and English translation thereof.

* cited by examiner

POWER MODULE SUBSTRATE, POWER MODULE SUBSTRATE WITH HEAT SINK, POWER MODULE, METHOD OF MANUFACTURING POWER MODULE SUBSTRATE, AND COPPER MEMBER-BONDING PASTE

TECHNICAL FIELD

The present invention relates to a power module substrate used in a semiconductor device for controlling a high current and a high voltage, a power module substrate with a heat sink, a power module, a method of manufacturing a power module substrate, and a copper member-bonding paste.

Priority is claimed on Japanese Patent Application No. 2012-020171, filed Feb. 1, 2012, Japanese Patent Application No. 2012-020172, filed Feb. 1, 2012, Japanese Patent Application No. 2012-267298, filed Dec. 6, 2012, and Japanese Patent Application No. 2012-267299, filed Dec. 6, 2012, the contents of which are incorporated herein by reference.

BACKGROUND ART

Among semiconductor elements, a power module for supplying power has a relatively high amount of heat generation. Therefore, as a substrate on which this power module is mounted, for example, a power module substrate including: a ceramic substrate that is formed of AlN (aluminum nitride), $Al_2O_3$ (alumina), or $Si_3N_4$ (silicon nitride); a circuit layer in which a first metal plate is bonded to one surface of the ceramic substrate; and a metal layer in which a second metal plate is bonded to the other surface of the ceramic substrate is used.

In such a power module substrate, a semiconductor element such as a power element is mounted on the circuit layer through a solder material.

PTL 1 discloses a power module substrate in which an aluminum plate is used as the first metal plate (circuit layer) and the second metal plate (metal layer).

PTLs 2 and 3 disclose a power module substrate in which a copper plate is used as the first metal plate (circuit layer) and the second metal plate (metal layer), and the copper plate is bonded to a ceramic substrate with an active metal method using an Ag—Cu—Ti-based brazing material.

CITATION LIST

Patent Literature

[PTL 1] Japanese Patent No. 3171234
[PTL 2] Japanese Unexamined Patent Application, First Publication No. S60-177634
[PTL 3] Japanese Patent No. 3211856

DISCLOSURE OF INVENTION

Technical Problem

In the power module substrate disclosed in PTL 1, the aluminum plate is used as the first metal plate forming the circuit layer. The thermal conductivity of aluminum is lower than that of copper. Therefore, when the aluminum plate is used as the circuit layer, heat generated from a heating element of an electrical components or the like mounted on the circuit layer cannot be spread and dissipated compared to a case where a copper plate is used. Therefore, when the power density is increased along with a decrease in the size and an increase in the power of an electronic component, there is a concern that heat may not be sufficiently dissipated.

In PTLs 2 and 3, since the circuit layer is formed using the copper plate, heat generated from a heating element of an electrical component or the like mounted on the circuit layer can be efficiently dissipated. As disclosed in PTLs 2 and 3, when the copper plate and the ceramic substrate are bonded with the active metal method, the Ag—Cu—Ti-based brazing material is melted by a reaction of Cu and Ag and solidified on a bonding portion between the copper plate and the ceramic substrate. As a result, the copper member and the ceramic member are bonded to each other, and an Ag—Cu eutectic structure layer is formed.

The Ag—Cu eutectic structure layer is extremely hard. Therefore, when a cooling-heating cycle is applied to the above-described power module substrate, and when a shearing stress is generated by a difference in thermal expansion coefficient between the ceramic substrate and the copper plate, there is a problem in that, for example, the ceramic substrate is cracked without the Ag—Cu eutectic structure layer being deformed.

The present invention has been made in consideration of the above-described circumstances, and an object thereof is to provide a power module substrate in which a copper plate formed of copper or a copper alloy is bonded to a ceramic substrate, and the cracking of the ceramic substrate can be suppressed during the application of a cooling-heating cycle; a power module substrate with a heat sink; a power module; a method of manufacturing a power module substrate; and a copper member-bonding paste.

Technical Solution

In order to solve the above-described problems, according to an aspect of the present invention, a power module substrate is provided, including: a copper plate that is formed of copper or a copper alloy and is laminated and bonded on a surface of a ceramic substrate; a nitride layer that is formed on the surface of the ceramic substrate between the copper plate and the ceramic substrate; and an Ag—Cu eutectic structure layer having a thickness of 15 μm or less that is formed between the nitride layer and the copper plate.

In this power module substrate, the thickness of the Ag—Cu eutectic structure layer formed in a bonding portion between the copper plate and the ceramic substrate is 15 μm or less. Therefore, even when a shearing stress is generated by a difference in thermal expansion coefficient between the ceramic substrate and the copper plate during the application of a cooling-heating cycle, the copper plate is appropriately deformed, and thus the cracking of the ceramic substrate can be suppressed. In addition, since the nitride layer is formed on the surface of the ceramic substrate, the ceramic substrate and the copper plate can be reliably bonded to each other.

It is preferable that the ceramic substrate be formed of either AlN or $Si_3N_4$. In this case, nitrogen and a nitride-forming element contained in the ceramic substrate react with each other. As a result, a nitride layer (which is formed of a nitride different from a nitride forming the ceramic substrate) is formed on the surface of the ceramic substrate, and thus the ceramic substrate and the nitride layer are strongly combined.

It is preferable that the nitride layer contain a nitride of one or two or more elements (nitride-forming elements) selected from Ti, Hf, Zr, and Nb. In this case, the ceramic substrate and the nitride layer are strongly combined, and thus the ceramic substrate and the copper plate can be strongly combined.

According to another aspect of the invention, a power module substrate with a heat sink is provided, including: the above-described power module substrate; and a heat sink that is bonded to the power module substrate and cools the power module substrate.

According to the heat sink-equipped power module substrate having the above-described configuration, heat generated from the power module substrate can be dissipated by the heat sink. Since the copper plate and the ceramic substrate are reliably bonded to each other, heat generated from the power module substrate can be reliably conducted to the heat sink side.

According to still another aspect of the present invention, a power module is provided, including: the above-described power module substrate; and an electronic component that is mounted on the power module substrate.

According to the power module having the above-described configuration, heat generated from an electronic component mounted on a circuit layer can be efficiently dissipated. In addition, even an increase in the power density (amount of heat generation) of an electronic component can be sufficiently handled.

According to still another aspect of the present invention, a method is provided of manufacturing a power module substrate including a copper plate that is formed of copper or a copper alloy and is laminated and bonded on a surface of a ceramic substrate, the method including: a copper member-bonding paste coating process of forming an Ag-nitride-forming element layer, which contains Ag and a nitride-forming element, on at least one of a bonding surface of the ceramic substrate and a bonding surface of the copper plate; a laminating process of laminating the ceramic substrate and the copper plate through the Ag-nitride-forming element layer; a heating process of pressing and heating a laminate of the ceramic substrate and the copper plate in a laminating direction to form a molten metal region at an interface between the ceramic substrate and the copper plate; and a solidification process of solidifying the molten metal region to bond the ceramic substrate and the copper plate to each other, in which in the heating process, Ag is diffused to the copper plate side to form the molten metal region at the interface between the ceramic substrate and the copper plate and to form a nitride layer on a surface of the ceramic substrate.

According to the method of manufacturing a power module substrate having the above-described configuration, in the heating process, Ag is diffused to the copper plate side to form the molten metal region at the interface between the ceramic substrate and the copper plate. Therefore, the thickness of the molten metal region can be suppressed to be small, and the thickness of the Ag—Cu eutectic structure layer formed in the molten metal region can be suppressed to be 15 µm or less. In the heating process, since a nitride layer is formed on a surface of the ceramic substrate, the ceramic substrate and the copper plate can be strongly bonded to each other. The thickness of the Ag—Cu eutectic structure layer may be, for example, 0.1 µm to 15 µm.

It is preferable that the nitride-forming element be one or two or more elements selected from Ti, Hf, Zr, and Nb. In this case, a nitride layer containing a nitride of Ti, Hf, Zr, or Nb can be formed on the surface of the ceramic substrate, and the ceramic substrate and the copper plate can be strongly bonded to each other. From the viewpoint of cost, Ti is a particularly preferable element.

It is preferable that, in the copper member-bonding paste coating process, one or two or more additional elements selected from In, Sn, Al, Mn, and Zn be added in addition to Ag and the nitride-forming element. In this case, since the melting point is decreased in the heating process, the molten metal region can be formed at a lower temperature, and thus the thickness of the Ag—Cu eutectic structure layer can be further reduced.

It is preferable that, in the copper member-bonding paste coating process, a paste containing Ag and a nitride-forming element be coated. In this case, an Ag-nitride-forming element layer can be reliably formed on at least one of a bonding surface of the ceramic substrate and a bonding surface of the copper plate.

The Ag-nitride-forming element layer-containing paste may contain a hydride of the nitride-forming element. In this case, since hydrogen of the hydride of the nitride-forming element functions as a reducing agent, an oxide film and the like formed on the surface of the copper plate can be removed, and the diffusion of Ag and the formation of the nitride layer can be reliably performed.

According to still another aspect of the present invention, a copper member-bonding paste is provided which is used when a copper member formed of copper or a copper alloy and a ceramic member are bonded to each other, the copper member-bonding paste including: a powder component containing Ag and a nitride-forming element; a resin; and a solvent, in which a composition of the powder component contains 0.4 mass % to 75 mass % of the nitride-forming element and a balance consisting of Ag and unavoidable impurities.

The copper member-bonding paste having the above-described configuration includes the powder component containing Ag and a nitride-forming element. Therefore, when the paste is coated on a bonding portion between the copper member and the ceramic member and is heated, Ag in the powder component is diffused to the copper member side such that a molten metal region is formed by a reaction of Cu and Ag. By the molten metal region being solidified, the copper member and the ceramic member are bonded to each other.

That is, since the molten metal region is formed by the diffusion of Ag to the copper member, the molten metal region is not formed to be thicker than necessary in the bonding portion, and the thickness of the Ag—Cu eutectic structure layer formed after the bonding (after the solidification) can be reduced. As such, since the thickness of the hard Ag—Cu eutectic structure layer is small, the cracking of the ceramic member can be suppressed.

In addition, since the composition of the powder component contains 0.4 mass % to 75 mass % of the nitride-forming element and a balance consisting of Ag and unavoidable impurities, a nitride layer can be formed on the surface of the ceramic member. As such, since the ceramic member and the copper member are bonded to each other through the nitride layer, the bonding strength between the ceramic substrate and the copper plate can be improved.

When the content of the nitride-forming element is less than 0.4 mass %, the nitride layer cannot be reliably formed, and there is a concern that the bonding strength between the ceramic substrate and the copper plate may be decreased. When the content of the nitride-forming element is greater than 75 mass %, the amount of Ag diffused to the copper member cannot be secured, and there is a concern that the ceramic substrate and the copper plate may not be joined to each other. Based on the above points, the content of the nitride-forming element in the powder component is set in a range from 0.4 mass % to 75 mass %.

The powder component may be a mixture of Ag powder and powder of the nitride-forming element or may be powder of an alloy of Ag and the nitride-forming element.

It is preferable that a particle size of powder forming the powder component be 40 μm or less. In this case, the copper member-joining paste can be coated to be thin. Accordingly, the thickness of the Ag—Cu eutectic structure layer formed after the bonding (after the solidification) can be further reduced. The particle size of the powder may be, for example, 0.01 μm to 40 μm.

It is preferable that the content of the powder component be 40 mass % to 90 mass %. In this case, since the content of the powder component is 40 mass % or greater, the molten metal region can be reliably formed by diffusing Ag to the copper member, and the copper member and the ceramic member can be bonded to each other. The nitride layer can be reliably formed on the surface of the ceramic member. On the other hand, since the content of the powder component is 90 mass % or less, the contents of the resin and the solvent can be secured, and the paste can be reliably coated in the bonding portion between the copper member and the ceramic member.

The powder component may contain a hydride of the nitride-forming element.

In this case, since hydrogen of the hydride of the nitride-forming element functions as a reducing agent, an oxide film and the like formed on the surface of the copper plate can be removed, and the diffusion of Ag and the formation of the nitride layer can be reliably performed.

Further, it is preferable that the powder component further contain one or two or more additional elements selected from In, Sn, Al, Mn, and Zn in addition to Ag and the nitride-forming element; and that the content of Ag be at least 25 mass % or greater.

In this case, the molten metal region can be formed at a lower temperature, unnecessary diffusion of Ag can be suppressed, and thus the thickness of the Ag—Cu eutectic structure layer can be further reduced.

It is preferable that the powder component further contain a dispersant in addition to the resin and the solvent. In this case, the powder component can be easily dispersed, Ag can be uniformly diffused, and the nitride layer can be uniformly formed.

It is preferable that the powder component further contain a plasticizer in addition to the resin and the solvent. In this case, a shape of the copper member-bonding paste can be relatively freely formed, and the paste can be reliably coated in the bonding portion between the copper member and the ceramic member.

It is preferable that the powder component further contain a reducing agent in addition to the resin and the solvent. In this case, due to the effect of the reducing agent, an oxide film and the like formed on the surface of the powder component can be removed, and the diffusion of Ag and the formation of the nitride layer can be reliably performed.

According to still another aspect of the present invention, a method of manufacturing a bonded body is provided in which a copper member formed of copper or a copper alloy and a ceramic member are bonded to each other, the method including: heating a laminate in which the copper member-bonding paste is interposed between the copper member and the ceramic member to bond the copper member and the ceramic member to each other.

In this case, a molten metal region can be formed by diffusing Ag, which is contained in the copper member-bonding paste, to the copper member side, and the copper member and the ceramic member can be bonded to each other by solidifying the molten metal region. Accordingly, since the thickness of the hard Ag—Cu eutectic structure layer is small, the cracking of the ceramic member can be suppressed.

A nitride layer can be formed on the surface of the ceramic member, and the bonding strength between the ceramic member and the copper member can be improved.

Advantageous Effects of Invention

According to the present invention, it is possible to provide a power module substrate in which a copper plate formed of copper or a copper alloy is bonded to a ceramic substrate, and the cracking of the ceramic substrate can be suppressed during the application of a cooling-heating cycle; a power module substrate with a heat sink; a power module; and a method of manufacturing a power module substrate.

In addition, it is possible to provide a copper member-bonding paste capable of suppressing, even when a copper member and a ceramic member are bonded to each other, the cracking of the ceramic member without increasing the thickness of a hard Ag—Cu eutectic structure layer and capable of reliably bonding the copper member and the ceramic member to each other; and a method of manufacturing a bonded body in which the copper member-bonding paste is used.

DESCRIPTION OF EMBODIMENTS

Hereinafter, a power module substrate, a power module substrate with a heat sink, and a power module according to embodiments of the present invention will be described with reference to the accompanying drawings.

First Embodiment

Figure 1:
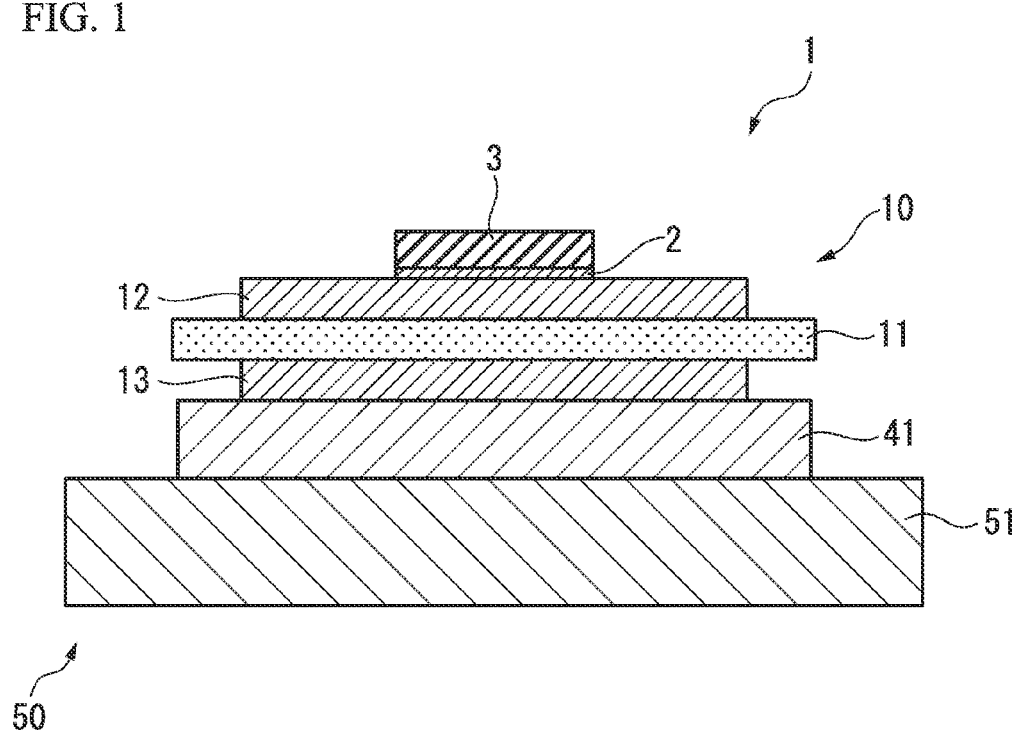
FIG. 1 is a cross-sectional view illustrating a power module substrate according to a first embodiment of the present invention; and a power module substrate with a heat sink and a power module in which the above-described power module substrate is used.

First, a first embodiment of the present invention will be described. FIG. 1 illustrates a power module substrate with a heat sink 50 and a power module 1 in which a power module substrate 10 according to the first embodiment is used.

The power module 1 includes the power module substrate 10 on which a circuit layer 12 is disposed; a semiconductor element 3 (electronic component) that is bonded to a surface of the circuit layer 12 through a solder layer 2; a buffer plate 41; and a heat sink 51. The solder layer 2 is formed of, for example, a Sn—Ag-based, Sn—In-based, or Sn—Ag—Cu-based solder material. In the embodiment, a Ni plating layer (not illustrated) is provided between the circuit layer 12 and the solder layer 2.

The power module substrate 10 includes a ceramic substrate 11; a circuit layer 12 that is disposed on one surface (upper surface in FIG. 1) of the ceramic substrate 11; and a metal layer 13 that is disposed on the other surface (lower surface in FIG. 1) of the ceramic substrate 11.

The ceramic substrate 11 prevents electric connection between the circuit layer 12 and the metal layer 13 and is formed of AlN (aluminum nitride) or $Si_3N_4$ (silicon nitride) having a high insulating property. The thickness of the ceramic substrate 11 is not limited but is preferably set to be in a range of 0.2 mm to 1.5 mm (in the embodiment, 0.635 mm).

Figure 5:
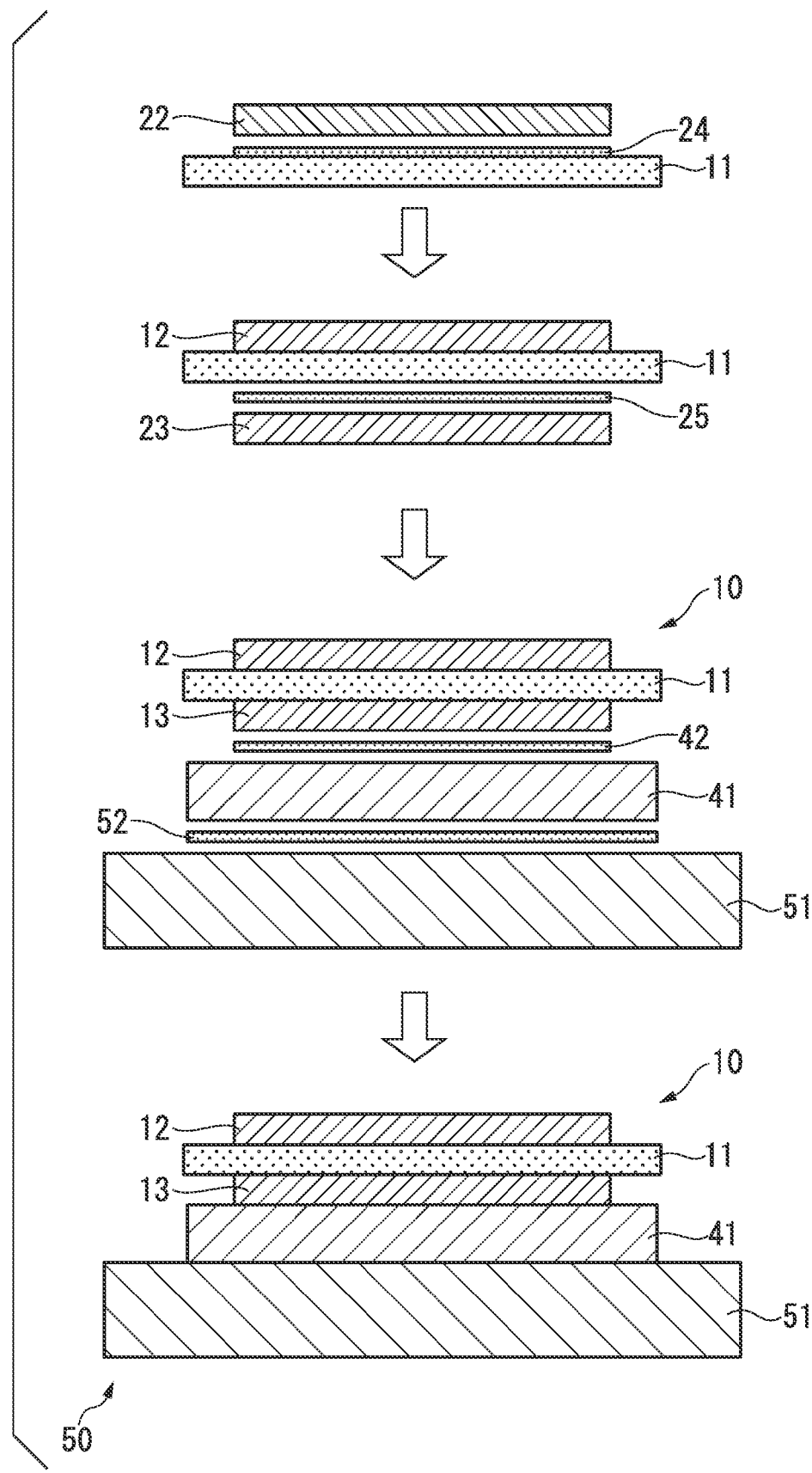
FIG. 5 is a cross-sectional view illustrating the method of manufacturing the power module substrate according to the first embodiment and the method of manufacturing a power module substrate with a heat sink in which the above-described power module substrate is used.

As illustrated in FIG. 5, the circuit layer 12 is formed by bonding a copper plate 22 to one surface (upper surface in FIG. 5) of the ceramic substrate 11. The thickness of the circuit layer 12 is not limited but is preferably set to be in a range of 0.1 mm to 1.0 mm (in the embodiment, 0.3 mm).

In the circuit layer 12, a circuit pattern is formed, and one surface (upper surface in FIG. 1) of the circuit layer 12 is a mounting surface on which the semiconductor element 3 is mounted.

In the embodiment, the copper plate 22 (circuit layer 12) is formed of a rolled sheet of oxygen-free copper (OFC) having a purity of 99.99 mass % or higher but may be formed of other copper alloys.

In order to bond the ceramic substrate 11 and the circuit layer 12 to each other, a copper member-bonding paste (described below) containing Ag and a nitride-forming element is used.

As illustrated in FIG. 5, the metal layer 13 is formed by bonding an aluminum plate 23 to the other surface (lower surface in FIG. 5) of the ceramic substrate 11. The thickness of the metal layer 13 is not limited but is preferably set to be in a range of 0.6 mm to 6.0 mm (in the embodiment, 0.6 mm).

In the embodiment, the aluminum plate 23 (metal layer 13) is formed of a rolled sheet of aluminum (so-called 4N aluminum) having a purity of 99.99 mass % or higher but may be optionally formed of other aluminum alloys.

The buffer plate 41 absorbs strains generated by a cooling-heating cycle and, as described in FIG. 1, is formed on the other surface (lower surface in FIG. 1) of the metal layer 13. The thickness of the buffer plate 41 is not limited but is preferably set to be in a range of 0.5 mm to 7.0 mm (in the embodiment, 0.9 mm).

In the embodiment, the buffer plate 41 is formed of a rolled sheet of aluminum (so-called 4N aluminum) having a purity of 99.99 mass % or higher but may be optionally formed of other aluminum alloys.

The heat sink 51 dissipates heat generated from the above-described power module substrate 10. The heat sink 51 according to the embodiment is bonded to the power module substrate 10 through the buffer plate 41.

In the embodiment, the heat sink 51 is formed of aluminum or an aluminum alloy. Specifically, the heat sink 51 is formed of a rolled sheet of an A6063 alloy but may be optionally formed of other aluminum alloys. The thickness of the heat sink 51 is not limited but is preferably set to be in a range of 1 mm to 10 mm (in the embodiment, 5 mm).

Figure 2:
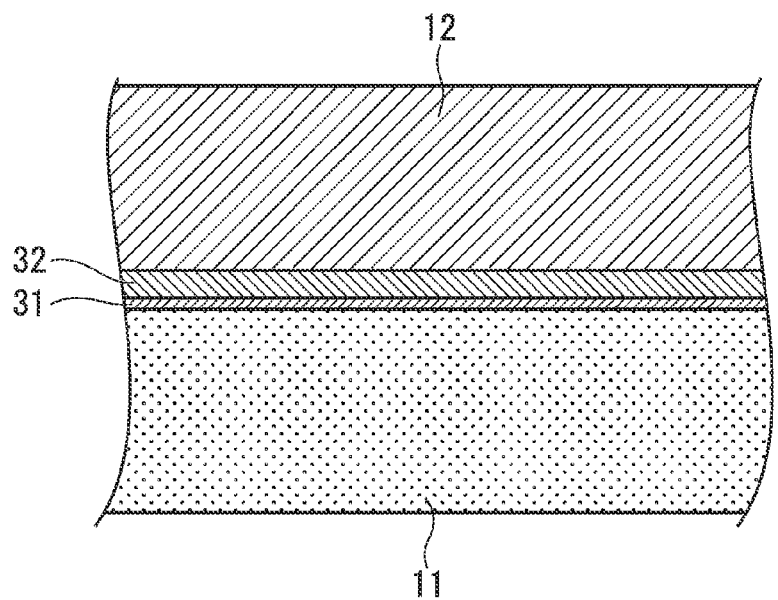
FIG. 2 is a cross-sectional view illustrating a bonding interface between a circuit layer and a ceramic substrate of FIG. 1.

FIG. 2 is an enlarged view illustrating a bonding interface between the ceramic substrate 11 and the circuit layer 12. On a surface of the ceramic substrate 11, a nitride layer 31 that is formed of a nitride of a nitride-forming element contained in the copper member-bonding paste is formed.

An Ag—Cu eutectic structure layer 32 is formed so as to be laminated on the nitride layer 31. The thickness of the Ag—Cu eutectic structure layer 32 is 15 μm or less. The thickness of the Ag—Cu eutectic structure layer can be measured from a backscattered electron image obtained using an EPMA (electron probe microanalyzer) and, for example, may be 0.1 μm to 15 μm.

Next, a method of manufacturing the power module substrate 10 having the above-described configuration and a method of manufacturing the heat sink-equipped power module substrate 50 will be described.

As described above, in order to bond the ceramic substrate 11 and the copper plate 22 which forms the circuit layer 12 to each other, the copper member-bonding paste containing Ag and the nitride-forming element is used. First, the copper member-bonding paste will be described.

The copper member-bonding paste includes a powder component containing Ag and a nitride-forming element, a resin, a solvent, a dispersant, a plasticizer, and a reducing agent. The dispersant, the plasticizer, and the reducing agent are optional components.

The content of the powder component in the entire copper member-bonding paste is 40 mass % to 90 mass %.

In the embodiment, the viscosity of the copper member-bonding paste is adjusted to be preferably 10 Pa·s to 500 Pa·s and more preferably 50 Pa·s to 300 Pa·s. In this range, the copper member-bonding paste is easily coated.

It is preferable that the nitride-forming element be one or two or more elements selected from Ti, Hf, Zr, and Nb. In the embodiment, Ti is contained as the nitride-forming element.

The composition of the powder component contains 0.4 mass % to 75 mass % of the nitride-forming element and a balance consisting of Ag and unavoidable impurities. The content of the nitride-forming element may be 0.2 mass % to 85 mass %. In the embodiment, the composition of the powder component contains 10 mass % of Ti and a balance consisting of Ag and unavoidable impurities.

In the embodiment, as the powder component containing Ag and the nitride-forming element (Ti), an alloy powder of Ag and Ti is used. The alloy powder is prepared using an atomizing method, and the particle size thereof can be set to be 40 μm or less, preferably 20 μm or less, and more preferably 10 μm or less by sieving the prepared alloy powder.

The particle size of the alloy powder can be measured using, for example, a laser diffraction scattering particle size analyzer.

The resin controls the viscosity of the copper member-bonding paste. For example, as the resin, ethyl cellulose, methyl cellulose, polymethyl methacrylate, acrylic resin, or alkyd resin can be used. The content of the resin in the paste may be, for example, 0.5 mass % to 25 mass %.

The solvent is a solvent for dissolving the above-described powder component. For example, as the solvent, methyl cellosolve, ethyl cellosolve, terpineol, toluene, texanol, or triethyl citrate can be used. The content of the solvent in the paste may be, for example, 5 mass % to 58 mass %.

The dispersant uniformly disperses the powder component. For example, as the dispersant, an anionic surfactant or a cationic surfactant can be used. The content of the dispersant in the paste may be, for example, 0.01 mass % to 5 mass %.

The plasticizer improves the formability of the copper member-bonding paste. For example, as the plasticizer, dibutyl phthalate or dibutyl adipate can be used. The content of the plasticizer in the paste may be, for example, 0.1 mass % to 20 mass %.

The reducing agent removes an oxide film or the like that is formed on a surface of the powder component. For example, rosin or abietic acid can be used. In the embodiment, abietic acid is used. The content of the reducing agent in the paste may be, for example, 0.5 mass % to 10 mass %.

The dispersant, the plasticizer, and the reducing agent may be optionally added. The copper member-bonding paste may be formed without adding the dispersant, the plasticizer, and the reducing agent.

Figure 3:
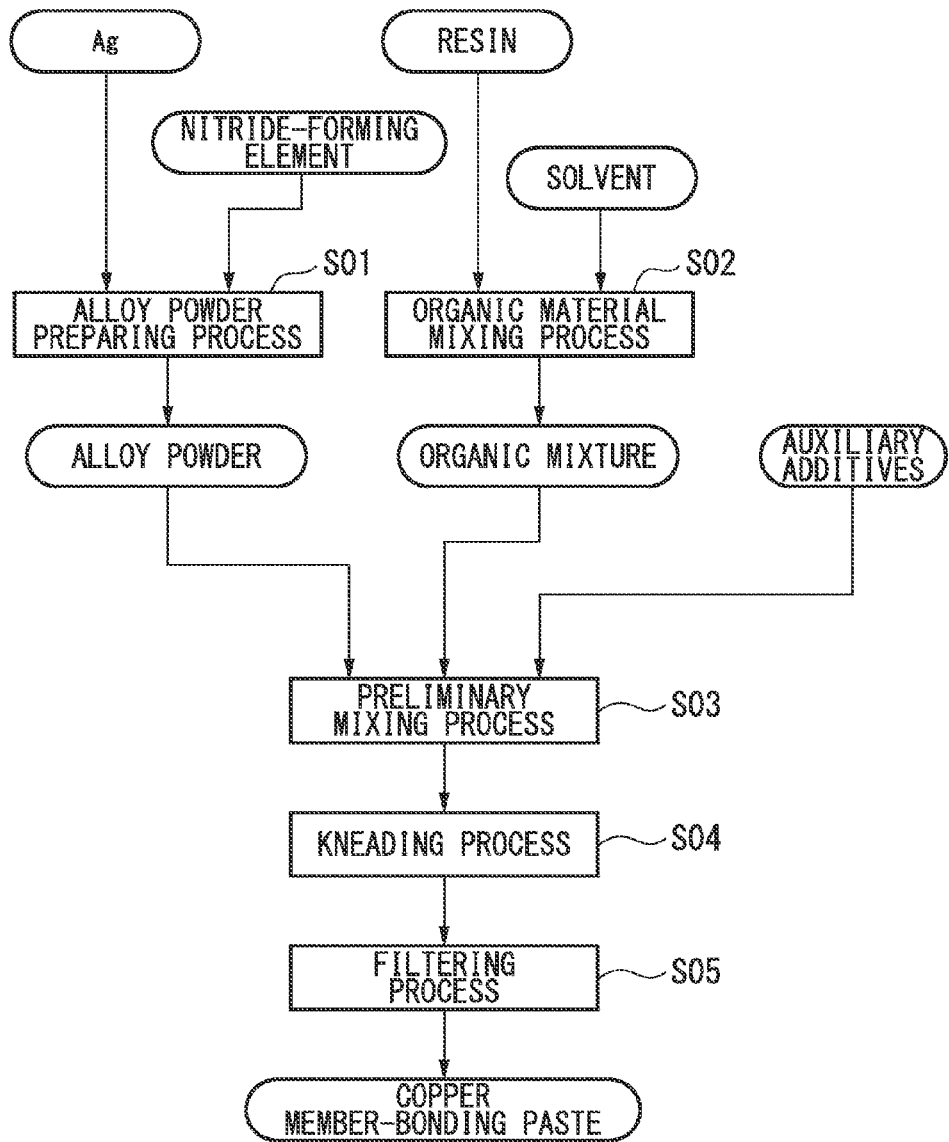
FIG. 3 is a flowchart illustrating a method of manufacturing a copper member-bonding paste which is used when a copper plate and a ceramic substrate are bonded to each other in the first embodiment.

A method of manufacturing the copper member-bonding paste will be described with reference to a flowchart of FIG. 3.

First, as described above, the alloy powder containing Ag and the nitride-forming element (Ti) is prepared using an atomizing method and is sieved to obtain an alloy powder having a particle size of 40 μm or less (alloy powder preparing process S01).

The solvent and the resin are mixed with each other to prepare an organic mixture (organic material mixing process S02).

The alloy powder obtained in the alloy powder preparing process S01, the organic mixture obtained in the organic material mixing process S02, and auxiliary additives such as the dispersant, the plasticizer, and the reducing agent are preliminarily mixed with each other using a mixer (preliminary mixing process S03).

Next, the preliminary mixture is mixed while being kneaded using a roll mill including plural rolls (kneading process S04).

The kneaded material obtained in the kneading process S04 is filtered using a paste filter (filtering process S05).

In this way, the above-described copper member-bonding paste is prepared.

Figure 4:
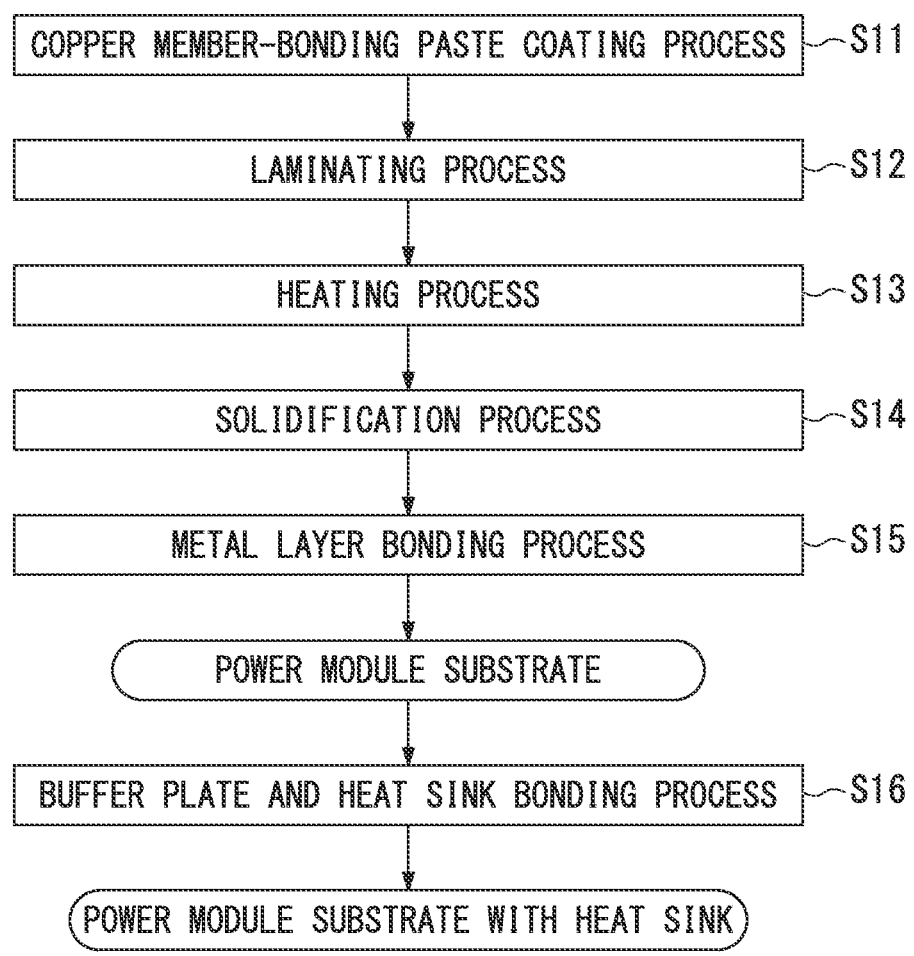
FIG. 4 is a flowchart illustrating a method of manufacturing the power module substrate according to the first embodiment and a method of manufacturing a power module substrate with a heat sink in which the above-described power module substrate is used.

Next, a method of manufacturing the power module substrate 10 according to the embodiment in which the copper member-bonding paste is used and a method of manufacturing the heat sink-equipped power module substrate 50 will be described with reference to FIGS. 4 to 6.

(Copper Member-Bonding Paste Coating Process S11)

As illustrated in FIG. 5, the above-described copper member-bonding paste is coated on one surface of the ceramic substrate 11 by, for example, screen printing, followed by drying. As a result, an Ag-nitride-forming element layer 24 is formed. The thickness of the Ag-nitride-forming element layer 24 is not particularly limited, but the thickness thereof after drying is preferably 20 μm to 300 μm.

(Laminating Process S12)

Next, the copper plate 22 is laminated on one surface of the ceramic substrate 11. That is, the Ag-nitride-forming element layer 24 is interposed between the ceramic substrate 11 and the copper plate 22.

(Heating Process S13)

Next, the copper plate 22 and the ceramic substrate 11 are charged into a vacuum heating furnace and heated while being pressed (pressure: 1 kgf/cm$^2$ to 35 kgf/cm$^2$) in a laminating direction. As a result, as illustrated in FIG. 6, Ag of the Ag-nitride-forming element layer 24 is diffused to the copper plate 22. At this time, a part of the copper plate 22 is melted by a reaction between Cu and Ag, and thus a molten metal region 27 is formed at an interface between the copper plate 22 and the ceramic substrate 11.

In the embodiment, it is preferable that the internal pressure of the vacuum heating furnace be set in a range of $10^{-6}$ Pa to $10^{-3}$ Pa and that the heating temperature be set in a range of 790° C. to 850° C.

(Solidification Process S14)

Next, the molten metal region 27 is cooled and solidified to bond the ceramic substrate 11 and the copper plate 22 to each other. After the completion of the solidification process S14, Ag of the Ag-nitride-forming element layer 24 is sufficiently diffused, and the Ag-nitride-forming element layer 24 does not remain at the bonding interface between the ceramic substrate 11 and the copper plate 22.

(Metal Layer Bonding Process S15)

Next, the aluminum plate 23 which forms the metal layer 13 is bonded to the other surface of the ceramic substrate 11. In the embodiment, as illustrated in FIG. 5, the aluminum plate 23 which forms the metal layer 13 is laminated on the other surface of the ceramic substrate 11 through a brazing foil 25 having a thickness of, preferably, 5 μm to 50 μm (in the embodiment, 14 μm). In the embodiment, the brazing foil 25 is preferably formed of an Al—Si-based brazing material containing Si, which is a melting point-lowering element.

Next, the ceramic substrate 11 and the aluminum plate 23 are charged into a heating furnace and heated while being pressed (preferably, pressure: 1 kgf/cm² to 35 kgf/cm²) in a laminating direction. As a result, the brazing foil 25 and a part of the aluminum plate 23 are melted, and thus a molten metal region is formed at an interface between the aluminum plate 23 and the ceramic substrate 11. It is preferable that the heating temperature be 600° C. to 650° C. and that the heating time be 30 minutes to 180 minutes.

Next, the molten metal region formed at the interface between the aluminum plate 23 and the ceramic substrate 11 is cooled and solidified to bond the ceramic substrate 11 and the aluminum plate 23 to each other. In this way, the power module substrate 10 according to the embodiment is manufactured.

(Buffer Plate-Heat Sink Bonding Process S16)

Next, as illustrated in FIG. 5, the buffer plate 41 and the heat sink 51 are laminated on the other surface (lower surface in FIG. 5) of the metal layer 13 of the power module substrate 10 through brazing foils 42 and 52, respectively.

In the embodiment, the brazing foils 42 and 52 have a thickness of, preferably, 5 µm to 50 µm (in the embodiment, 14 µm) and are formed of an Al—Si-based brazing material containing Si, which is a melting point-lowering element.

Next, the power module substrate 10, the buffer plate 41, and the heat sink 51 are charged into a heating furnace and heated while being pressed (preferably, pressure: 1 kgf/cm² to 35 kgf/cm²) in a laminating direction. As a result, molten metal regions are formed at an interface between the metal layer 13 and the buffer plate 41 and at an interface between the buffer plate 41 and the heat sink 51, respectively. It is preferable that the heating temperature be 550° C. to 610° C. and that the heating time be 30 minutes to 180 minutes.

Next, the molten metal regions which are formed at the interface between the metal layer 13 and the buffer plate 41 and at the interface between the buffer plate 41 and the heat sink 51 are solidified to bond the power module substrate 10, the buffer plate 41, and the heat sink 51 to each other. As a result, the heat sink-equipped power module substrate 50 according to the embodiment is manufactured.

The semiconductor element 3 is placed on a surface of the circuit layer 12 through a solder material and is soldered thereto in a reducing furnace. As a result, the power module 1 in which the semiconductor element 3 is bonded to the circuit layer 12 through the solder layer 2 is manufactured.

According to the power module substrate 10 according to the embodiment having the above-described configuration, in a bonding portion between the circuit layer 12 which is formed of the copper plate 22 and the ceramic substrate 11, the thickness of the Ag—Cu eutectic structure layer 32 is 15 µm or less. Therefore, even when a shearing stress is generated by a difference in thermal expansion coefficient between the ceramic substrate 11 and the circuit layer 12 during the application of a cooling-heating cycle, the circuit layer 12 is appropriately deformed, and thus the cracking of the ceramic substrate 11 can be suppressed.

In addition, since the nitride layer 31 is formed on the surface of the ceramic substrate 11, the ceramic substrate 11 and the circuit layer 12 can be reliably bonded to each other.

In the embodiment, since the ceramic substrate 11 is formed of AlN, the nitride-forming element contained in the copper member-bonding paste reacts with the ceramic substrate 11. As a result, the nitride layer 31 is formed on the surface of the ceramic substrate 11, and thus the ceramic substrate 11 and the nitride layer 31 are strongly combined.

Further, the nitride layer 31 contains a nitride of one or two or more elements selected from Ti, Hf, Zr, and Nb. Specifically, in the embodiment, the nitride layer 31 contains TiN. Therefore, the ceramic substrate 11 and the nitride layer 31 are strongly combined, and thus the ceramic substrate 11 and the circuit layer 12 are strongly combined.

In the heat sink-equipped power module substrate 50 and the power module 1 according to the embodiment, heat generated from the power module substrate 10 can be dissipated by the heat sink 51. Since the circuit layer 12 and the ceramic substrate 11 are reliably bonded to each other, heat which is generated from the semiconductor element 3 mounted on the mounting surface of the circuit layer 12 can be reliably conducted to the heat sink 51 side, and an increase in the temperature of the semiconductor element 3 can be suppressed. Accordingly, even an increase in the power density (amount of heat generation) of the semiconductor element 3 can be sufficiently handled.

Further, in the heat sink-equipped power module substrate 50 and the power module 1, the buffer plate 41 is disposed between the power module substrate 10 and the heat sink 51. Therefore, strains generated by a difference in thermal expansion coefficient between the power module substrate 10 and the heat sink 51 can be absorbed by the deformation of the buffer plate 41.

In addition, in the heating process S13 of the manufacturing method according to the embodiment, Ag is diffused to the copper plate 22 side to form the molten metal region 27 at the interface between the ceramic substrate 11 and the copper plate 22. Therefore, the thickness of the molten metal region 27 can be suppressed to be small, and the thickness of the Ag—Cu eutectic structure layer 32 can be suppressed to be 15 µm or less. Further, in the heating process S13, since the nitride layer 31 is formed on the surface of the ceramic substrate 11, the ceramic substrate 11 and the copper plate 22 can be strongly bonded to each other.

In addition, in the embodiment, Ti is contained as the nitride-forming element. Therefore, the ceramic substrate 11 formed of AlN and Ti react with each other to form the nitride layer 31. As a result, the ceramic substrate 11 and the copper plate 22 can be reliably bonded to each other.

Further, in the embodiment, in the copper member-bonding paste coating process S11, the copper member-bonding paste containing Ag and the nitride-forming element is coated. Therefore, the Ag-nitride-forming element layer 24 can be reliably formed on the bonding surface of the ceramic substrate 11.

In the copper member-bonding paste used in the embodiment, the composition of the powder component contains 0.4 mass % to 75 mass % of the nitride-forming element and a balance consisting of Ag and unavoidable impurities. Therefore, the nitride layer 31 can be formed on the surface of the ceramic substrate 11. As such, since the ceramic substrate 11 and the circuit layer 12 which is formed of the copper plate 22 are bonded to each other through the nitride layer 31, the bonding strength between the ceramic substrate 11 and the circuit layer 12 can be improved.

In the embodiment, the particle size of the powder forming the powder component, that is, the particle size of the alloy powder containing Ag and the nitride-forming element (Ti) is 40 µm or less. Therefore, the copper member-bonding paste can be coated to be thin. Accordingly, the thickness of the Ag—Cu eutectic structure layer 32 formed after the bonding (after the solidification) can be reduced.

Since the content of the powder component is 40 mass % to 90 mass %, the molten metal region 27 can be reliably formed by diffusing Ag to the copper plate 22, and the copper plate 22 and the ceramic substrate 11 can be bonded to each other. In addition, the content of the solvent can be secured, the copper member-bonding paste can be reliably coated on the bonding surface of the ceramic substrate 11, and the Ag-nitride-forming element layer 24 can be reliably formed.

In the embodiment, since the dispersant is optionally contained, the powder component can be easily dispersed, and Ag can be uniformly diffused. The nitride layer 31 can be uniformly formed.

Further, in the embodiment, since the plasticizer is optionally contained, the shape of the copper member-bonding paste can be relatively freely formed, and the paste can be reliably coated in the bonding portion of the ceramic substrate 11.

In the embodiment, since the reducing agent is optionally contained, due to the effect of the reducing agent, an oxide film and the like formed on the surface of the powder component can be removed, and the diffusion of Ag and the formation of the nitride layer 31 can be reliably performed.

Second Embodiment

Figure 7:
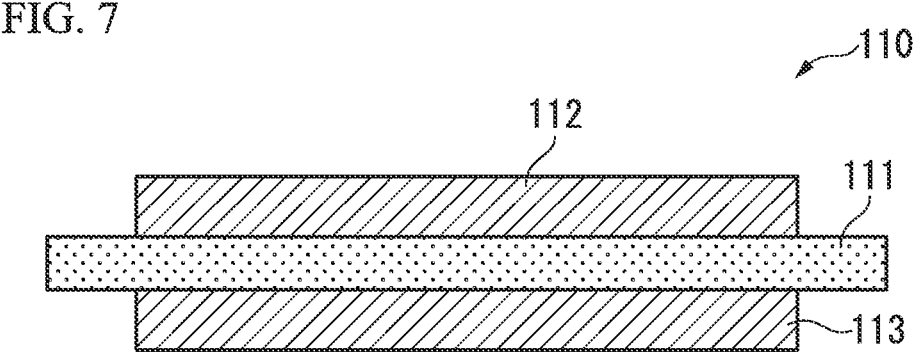
FIG. 7 is a cross-sectional view illustrating a power module substrate according to a second embodiment of the present invention.

Next, a second embodiment of the present invention will be described. FIG. 7 illustrates a power module substrate 110 according to the embodiment. This power module substrate 110 includes a ceramic substrate 111, a circuit layer 112 that is disposed on one surface (upper surface in FIG. 7) of the ceramic substrate 111, and a metal layer 113 that is disposed on the other surface (lower surface in FIG. 7) of the ceramic substrate 111.

The ceramic substrate 111 prevents electric connection between the circuit layer 112 and the metal layer 113 and is formed of $Si_3N_4$ (silicon nitride) having a high insulating property. The thickness of the ceramic substrate 111 is preferably set to be in a range of 0.2 mm to 1.5 mm (in the embodiment, 0.32 mm).

Figure 10:
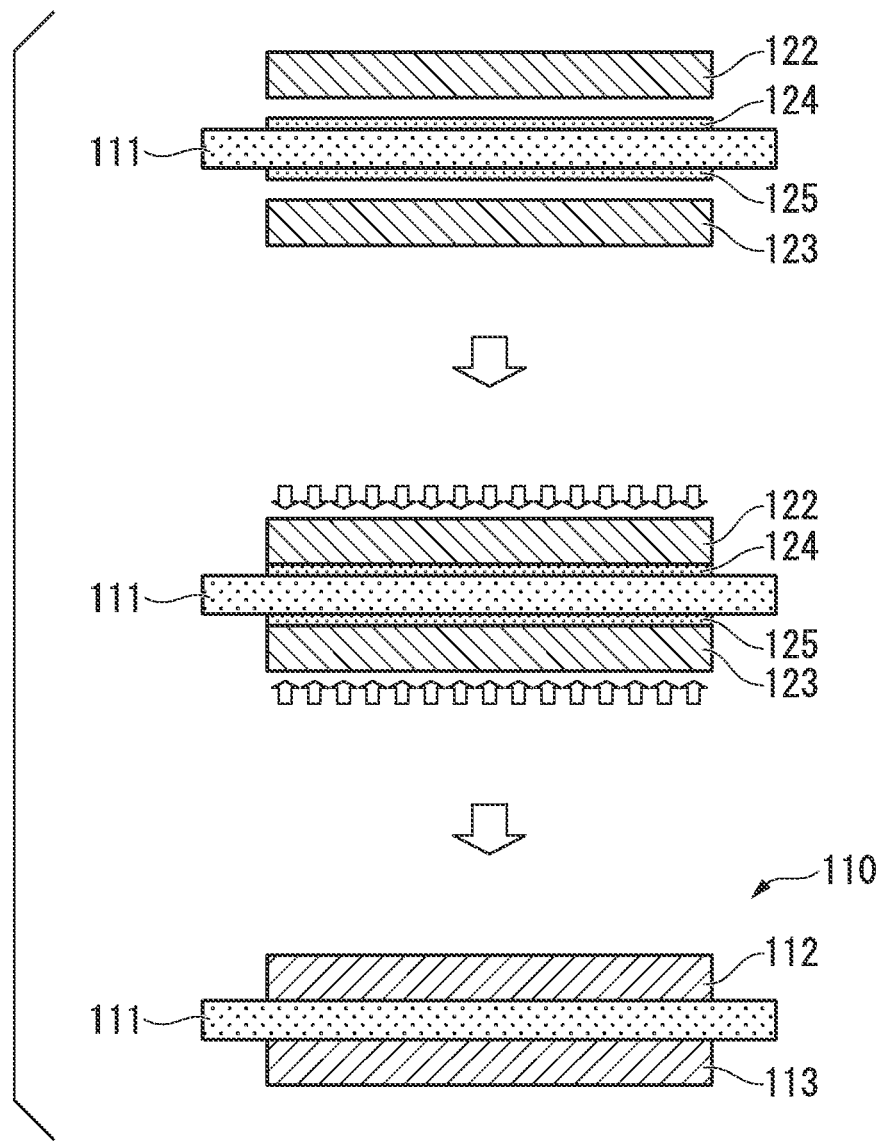
FIG. 10 is a cross-sectional view illustrating the method of manufacturing the power module substrate according to the second embodiment.

As illustrated in FIG. 10, the circuit layer 112 is formed by bonding a copper plate 122 to one surface (upper surface in FIG. 10) of the ceramic substrate 111. The thickness of the circuit layer 112 is preferably set to be in a range of 0.1 mm to 1.0 mm (in the embodiment, 0.6 mm) In the circuit layer 112, a circuit pattern is formed, and one surface (upper surface in FIG. 7) of the circuit layer 112 is a mounting surface on which a semiconductor element is mounted.

In the embodiment, the copper plate 122 (circuit layer 112) is formed of a rolled sheet of oxygen-free copper (OFC) having a purity of, preferably, 99.99 mass % or higher.

As illustrated in FIG. 10, the metal layer 113 is formed by bonding a copper plate 123 to the other surface (lower surface in FIG. 10) of the ceramic substrate 111. The thickness of the metal layer 113 is preferably set to be in a range of 0.1 mm to 1.0 mm (in the embodiment, 0.6 mm).

In the embodiment, the copper plate 123 (metal layer 113) is formed of a rolled sheet of oxygen-free copper (OFC) having a purity of, preferably, 99.99 mass % or higher.

In order to bond the ceramic substrate 111 and the circuit layer 112 to each other and to bond the ceramic substrate 111 and the metal layer 113 to each other, a copper member-bonding paste (described below) containing Ag and a nitride-forming element is used.

Figure 8:
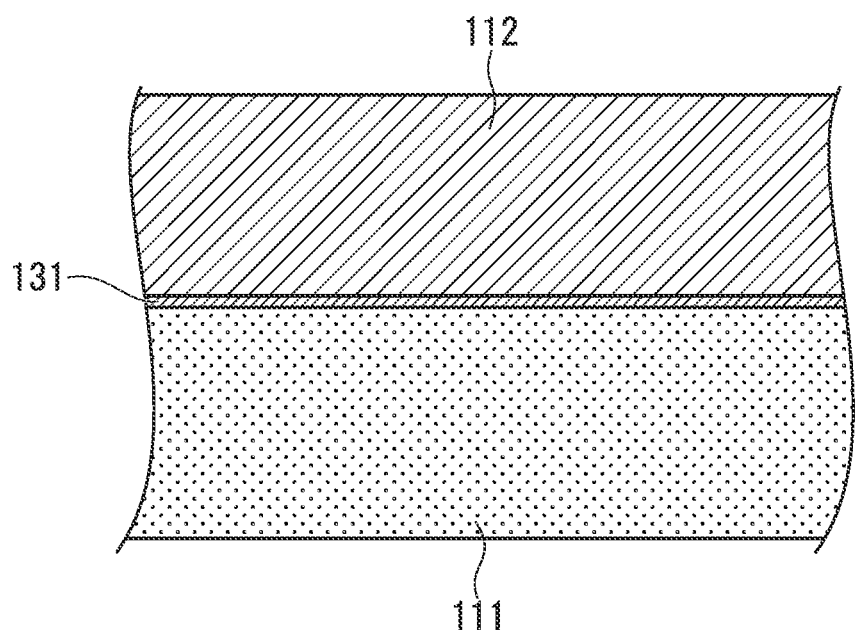
FIG. 8 is a cross-sectional view illustrating bonding interfaces between a circuit layer and a ceramic substrate and between a metal layer and the ceramic substrate in FIG. 7.

FIG. 8 is an enlarged view illustrating bonding interfaces between the ceramic substrate 111 and the circuit layer 112 and between the ceramic substrate 111 and the metal layer 113. On a surface of the ceramic substrate 111, a nitride layer 131 that is formed of a nitride of a nitride-forming element contained in the copper member-bonding paste is formed.

In the embodiment, an Ag—Cu eutectic structure layer observed in the first embodiment is not clearly observed.

Next, a method of manufacturing the power module substrate 110 having the above-described configuration will be described. In order to bond the ceramic substrate 111 and the copper plate 122 which forms the circuit layer 112 to each other, the copper member-bonding paste containing Ag and the nitride-forming element is used. First, the copper member-bonding paste will be described.

The copper member-bonding paste used in the embodiment includes a powder component containing Ag and a nitride-forming element, a resin, a solvent, a dispersant, a plasticizer, and a reducing agent.

The powder component contains one or two or more additional elements selected from In, Sn, Al, Mn, and Zn in addition to Ag and the nitride-forming element. In the embodiment, the powder component contains Sn.

The content of the powder component in the entire copper member-bonding paste be 40 mass % to 90 mass %.

In the embodiment, the viscosity of the copper member-bonding paste is adjusted to be preferably 10 Pa·s to 500 Pa·s and more preferably 50 Pa·s to 300 Pa·s.

It is preferable that the nitride-forming element be one or two or more elements selected from Ti, Hf, Zr, and Nb. In the embodiment, Zr is contained as the nitride-forming element.

In the composition of the powder component, the content of the nitride-forming element (in the embodiment, Zr) is 0.4 mass % to 75 mass %, the content of one or two or more additional elements (in the embodiment, Sn) selected from In, Sn, Al, Mn, and Zn is 0 mass % to 50 mass %, and a balance consists of Ag and unavoidable impurities. In this case, the content of Ag is 25 mass % or greater. In the embodiment, the composition of the powder component contains 40 mass % of Zr, 20 mass % of Sn, and a balance consisting of Ag and unavoidable impurities.

In the embodiment, as the powder element, element powders (Ag powder, Zr powder, Sn powder) are used. The Ag powder, the Zr powder, and the Sn powder are mixed with each other such that the entire powder component has the above-described composition.

The particle size of each of the Ag powder, the Zr powder, and the Sn powder is set to be 40 μm or less, preferably 20 μm or less, and more preferably 10 μm or less. The particle size of each of the Ag powder, the Zr powder, and the Sn powder can be measured using, for example, a laser diffraction scattering particle size analyzer.

As the resin and the solvent, the same materials as those of the first embodiment are used. In the embodiment, the dispersant, the plasticizer, and the reducing agent are optionally added.

The copper member-bonding paste used in the embodiment is manufactured according to the manufacturing method described in the first embodiment. That is, the copper member-bonding paste is manufactured in the same procedure as that of the first embodiment, except that the Ag powder, the Zr powder, and the Sn powder are used instead of the alloy powder.

Figure 9:
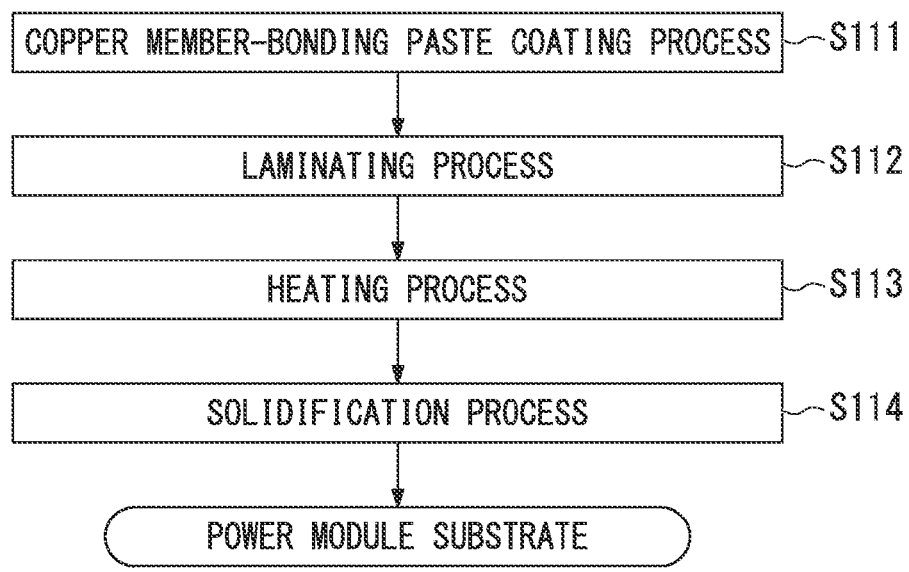
FIG. 9 is a flowchart illustrating a method of manufacturing the power module substrate according to the second embodiment.

Next, a method of manufacturing the power module substrate 110 according to the embodiment in which the copper member-bonding paste is used will be described with reference to FIGS. 9 and 10.

(Copper Member-bonding paste Coating Process S111)

First, as illustrated in FIG. 10, the copper member-bonding paste according to the above-described embodiment is coated on one surface and the other surface of the ceramic substrate 111 by, for example, screen printing. As a result, Ag-nitride-forming element layers 124 and 125 are formed. The thickness of each of the Ag-nitride-forming element layers 124 and 125 after drying is preferably 20 μm to 300 μm.

(Laminating Process S112)

Next, the copper plate 122 is laminated on one surface of the ceramic substrate 111. The copper plate 123 is laminated on the other surface of the ceramic substrate 111. That is, the Ag-nitride-forming element layers 124 and 125 are interposed between the ceramic substrate 111 and the copper plate 122 and between the ceramic substrate 111 and the copper plate 123, respectively.

(Heating Process S113)

Next, the copper plate 122, the ceramic substrate 111, and the copper plate 123 are charged into a vacuum heating furnace and heated while being pressed (preferably, pressure: 1 kgf/cm$^2$ to 35 kgf/cm$^2$) in a laminating direction. As a result, Ag of the Ag-nitride-forming element layer 124 is diffused to the copper plate 122, and Ag of the Ag-nitride-forming element layer 125 is diffused to the copper plate 123.

At this time, Cu and Ag of the copper plate 122 are melted by a reaction, and thus a molten metal region is formed at an interface between the copper plate 122 and the ceramic substrate 111. Cu and Ag of the copper plate 123 are melted by a reaction, and thus a molten metal region is formed at an interface between the copper plate 123 and the ceramic substrate 111.

In the embodiment, it is preferable that the internal pressure of the vacuum heating furnace be set in a range of $10^{-6}$ Pa to $10^{-3}$ Pa and that the heating temperature be set in a range of 790° C. to 850° C.

(Solidification Process S114)

Next, the molten metal regions are solidified to bond the ceramic substrate 111 and the copper plates 122 and 123 to each other. After the completion of the solidification process S114, Ag of the Ag-nitride-forming element layers 124 and 125 is sufficiently diffused, and the Ag-nitride-forming element layers 124 and 125 do not remain at the bonding interfaces between the ceramic substrate 111 and the copper plates 122 and 123.

As such, the power module substrate 110 according to the embodiment is manufactured. In the power module substrate 110, a semiconductor element is mounted on the circuit layer 112, and a heat sink is disposed on the other surface of the metal layer 113.

According to the power module substrate 110 according to the embodiment having the above-described configuration, in a bonding portion between the circuit layer 112 which is formed of the copper plate 122 and the ceramic substrate 111, the thickness of each of the Ag—Cu eutectic structure layers is 15 μm or less. In the embodiment, the Ag—Cu eutectic structure layers are not clearly observed. Therefore, even when a shearing stress is generated by a difference in thermal expansion coefficient between the ceramic substrate 111 and the circuit layer 112 during the application of a cooling-heating cycle, the circuit layer 112 is appropriately deformed, and thus the cracking of the ceramic substrate 111 can be suppressed. In addition, since the nitride layer 131 is formed on the surface of the ceramic substrate 111, the ceramic substrate 111 and the circuit layer 112 can be reliably bonded to each other.

In addition, since the molten metal regions are formed by the diffusion of Ag to the copper plates 122 and 123, the molten metal regions are not formed to be thicker than necessary in the bonding portions between the ceramic substrate 111 and the copper plates 122 and 123, and the thickness of each of the Ag—Cu eutectic structure layers formed after the bonding (after the solidification) can be reduced. Accordingly, the cracking of the ceramic substrate 111 can be suppressed.

In addition, in the embodiment, Zr is contained as the nitride-forming element. Therefore, the ceramic substrate 111 formed of $Si_3N_4$ and Zr react with each other to form the nitride layer 131. As a result, the ceramic substrate 111 and the copper plates 122 and 123 can be reliably bonded to each other.

In the embodiment, as the powder component, one or two or more additional elements (in the embodiment, Sn) selected from In, Sn, Al, Mn, and Zn are contained in addition to Ag and the nitride-forming element (in the embodiment, Zr). Therefore, the molten metal regions can be formed at a lower temperature, and thus the thickness of each of the formed Ag—Cu eutectic structure layers can be further reduced.

According to the method of manufacturing the copper member-bonding paste according to the embodiment and the method of manufacturing a bonded body which have the above-described configuration, Ag can be interposed at the interface between the ceramic substrate 111 and the copper plate 122 and at the interface between the ceramic substrate 111 and the copper plate 123. By diffusing Ag to the copper plates 122 and 123, the molten metal regions can be formed by a reaction between Cu and Ag. By solidifying the molten metal regions, the ceramic substrate 111 and the copper plates 122 and 123 can be bonded to each other.

Hereinabove, the embodiments of the present invention have been described. However, the present invention is not limited thereto, and various appropriate modifications can be made within a range not departing from the technical ideas of the present invention.

For example, in the above description, Ti or Zr is used as the nitride-forming element. However, the nitride-forming element is not limited to Ti or Zr, and other nitride-forming elements such as Hf or Nb may also be used.

The powder component contained in the Ag-nitride-forming element layer-containing paste (copper member-bonding paste) may contain a hydride of the nitride-forming element such as $TiH_2$ or $ZrH_2$. In this case, since hydrogen of the hydride of the nitride-forming element functions as a reducing agent, an oxide film and the like formed on the surface of the copper plate can be removed, and the diffusion of Ag and the formation of the nitride layer can be reliably performed.

In the description of the second embodiment, Sn is added as the additional element. However, the additional element is not limited to Sn, and one or two or more additional elements selected from In, Sn, Al, Mn, and Zn may also be used.

In the above description, the particle size of the powder forming the powder component is 40 μm or less. However, the particle size is not particularly limited to 40 μm or less.

In the above description, the dispersant, the plasticizer, and the reducing agent are contained. However, the present invention is not limited to this configuration, and the above components may not be contained. The dispersant, the plasticizer, and the reducing agent are optionally added.

Further, in the above description, the aluminum plate and the ceramic substrate or the aluminum plates are bonded to each other by brazing. However, the bonding method is not limited to brazing, and casting, metal pasting, or the like may also be used. An aluminum plate and a ceramic substrate, an aluminum plate and a top plate, or other aluminum materials may be bonded to each other using transient liquid phase bonding by disposing Cu, Si, Zn, Ge, Ag, Mg, Ca, Ga, or Li therebetween.

Figure 6:
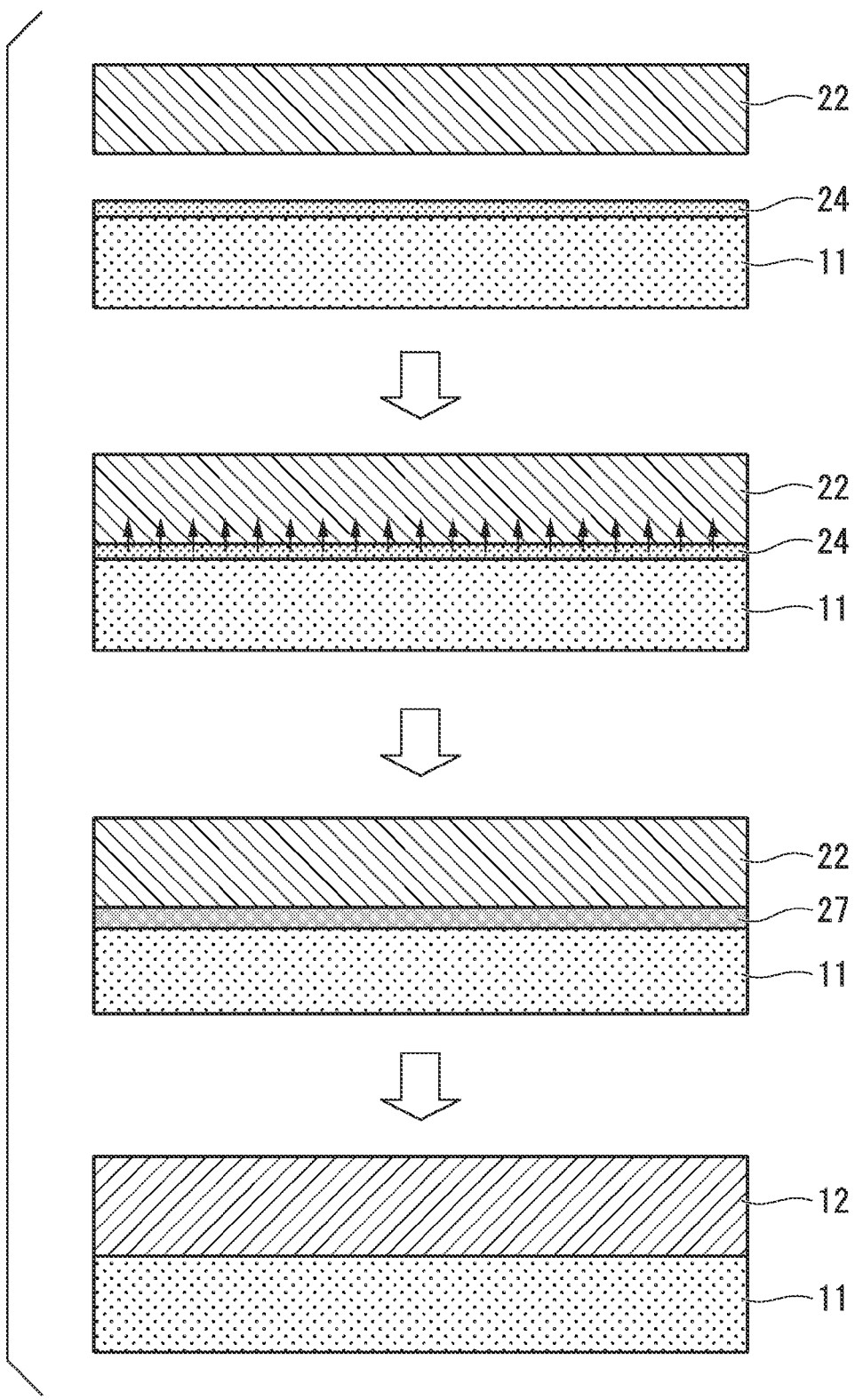
FIG. 6 is a cross-sectional view illustrating a process of bonding a ceramic substrate and a copper plate to each other.

The present invention is not limited to the power module substrate and the heat sink-equipped power module substrate which are manufactured using the manufacturing methods of FIGS. 5, 6, and 10. A power module substrate and the like which are manufactured using other manufacturing methods may also be used.

Figure 11:
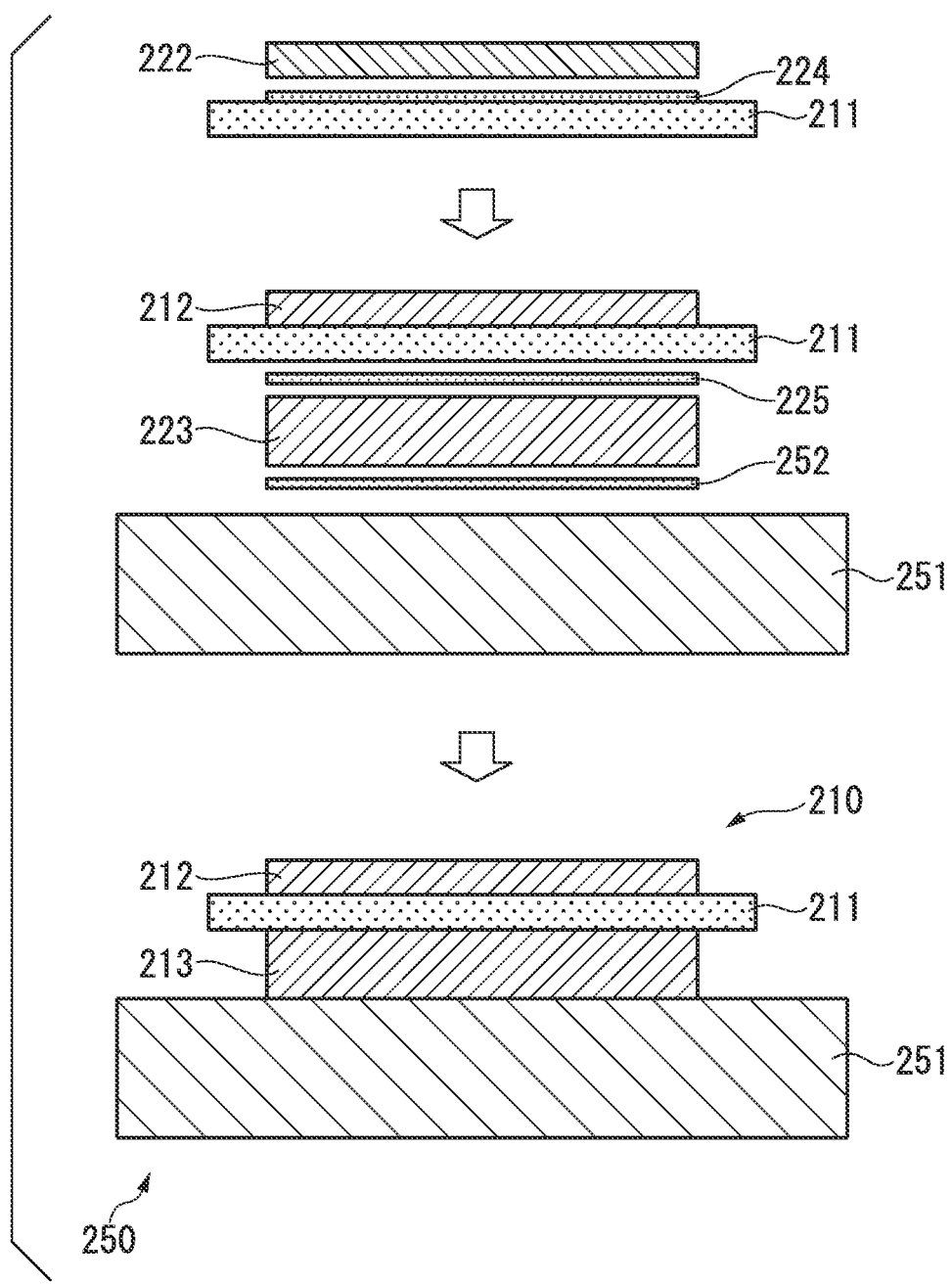
FIG. 11 is a cross-sectional view illustrating a method of manufacturing a power module substrate according to another embodiment of the present invention and a method of manufacturing a power module substrate with a heat sink in which the above-described power module substrate is used.

For example, as illustrated in FIG. 11, a configuration may also be adopted in which a copper plate 222 which forms a circuit layer 212 is bonded to one surface of a ceramic substrate 211 through an Ag-nitride-forming element layer 224, an aluminum plate 223 which forms a metal layer 213 is bonded to the other surface of the ceramic substrate 211 through a brazing foil 225, and a heat sink 251 is bonded to the other surface of the aluminum plate 223 through a brazing foil 252. As such, a power module substrate with a heat sink 250 including a power module substrate 210 and a heat sink 251 is manufactured.

Figure 12:
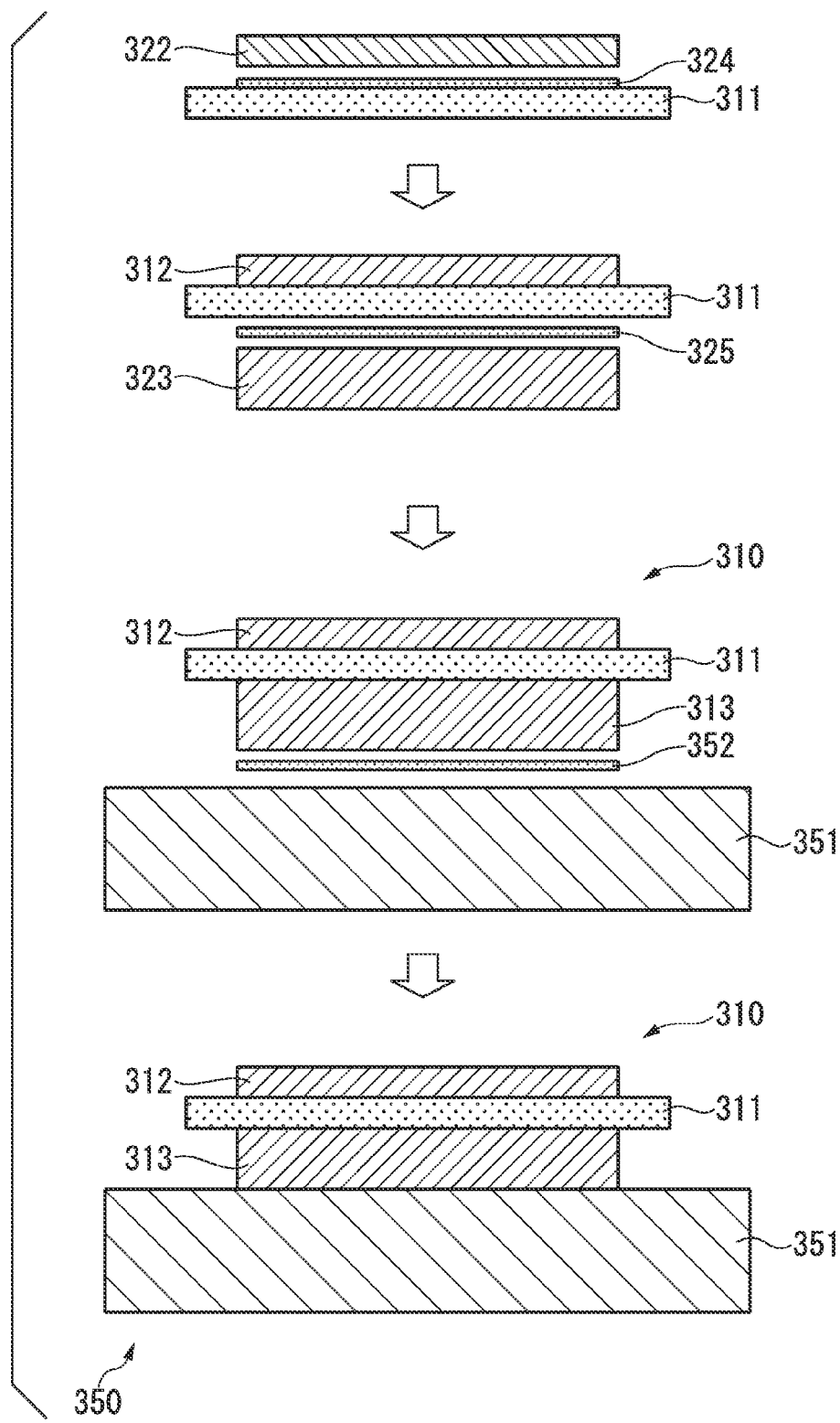
FIG. 12 is a cross-sectional view illustrating a method of manufacturing a power module substrate according to still another embodiment of the present invention and a method of manufacturing a power module substrate with a heat sink in which the above-described power module substrate is used.

As illustrated in FIG. 12, a power module substrate 310 may be manufactured by bonding a copper plate 322 which forms a circuit layer 312 to one surface of a ceramic substrate 311 through an Ag-nitride-forming element layer 324 and bonding an aluminum plate 323 which forms a metal layer 313 to the other surface of the ceramic substrate 311 through a brazing foil 325. Next, a heat sink 351 may be bonded to the other surface of the metal layer 313 through a brazing foil 352. As such, a power module substrate with a heat sink 350 including a power module substrate 310 and a heat sink 351 is manufactured.

Figure 13:
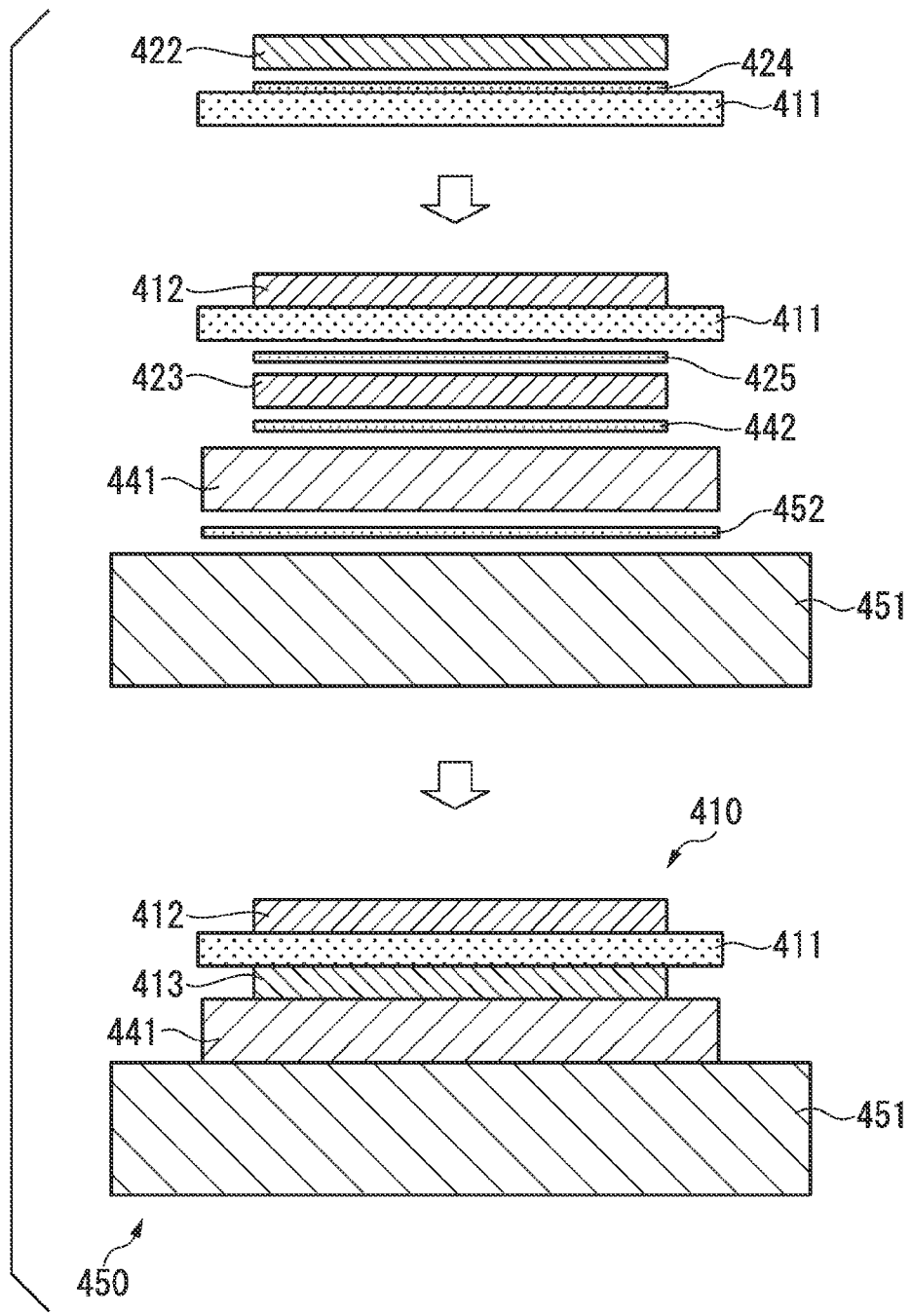
FIG. 13 is a cross-sectional view illustrating a method of manufacturing a power module substrate according to still another embodiment of the present invention and a method of manufacturing a power module substrate with a heat sink in which the above-described power module substrate is used.

Further, as illustrated in FIG. 13, a configuration may also be adopted in which a copper plate 422 which forms a circuit layer 412 is bonded to one surface of a ceramic substrate 411 through an Ag-nitride-forming element layer 424, an aluminum plate 423 which forms a metal layer 413 is bonded to the other surface of the ceramic substrate 411 through a brazing foil 425, a buffer plate 441 is bonded to the other surface of the aluminum plate 423 through a brazing foil 442, and a heat sink 451 is bonded to the other surface of the buffer plate 441 through a brazing foil 452. As such, a power module substrate with a heat sink 450 including a power module substrate 410, the buffer plate 441, and the heat sink 451 is manufactured.

In the above description, the copper member-bonding paste according to the embodiment is used when the ceramic substrate and the copper plate are bonded to each other. However, the present invention is not limited to this configuration, and the copper member-bonding paste according to the invention may be used when a ceramic member and a copper member are bonded to each other.

EXAMPLES

A comparative test which was performed to confirm the effectiveness of the present invention will be described. Various pastes were prepared under conditions shown in Tables 1, 2, and 3. In Table 1, an alloy powder was used as the powder component. In Table 2, powders (element powders) of the respective elements were used as the powder component. In Table 3, powders (element powders) of the respective elements were used as the powder component, and powder of a hydride of the nitride-forming element was used as the nitride-forming element. Table 3 shows the content of the nitride-forming element (content of active metal) as well as a mixing ratio of the element powder of the hydride of the nitride-forming element.

An anionic surfactant was used as a dispersant, dibutyl adipate was used as a plasticizer, and abietic acid was used as a reducing agent.

A mixing ratio of the resin, the solvent, the dispersant, the plasticizer, and the reducing agent aside from the powder component is 7:70:3:5:15 (resin:solvent:dispersant:plasticizer:reducing agent) by mass ratio.

TABLE 1

| | | Alloy Powder Mixing Ratio/wt % | | | | | | | | | | Maximum Particle Size in Alloy Powder/μm | Ratio of Powder Component in Paste |
|---|---|---|---|---|---|---|---|---|---|---|---|---|---|
| | | Ag | Cu | Ti | Zr | Hf | Nb | In | Sn | Mn | Al | Zn | | |
| Example | 1 | 25 | | 75 | | | | | | | | | <5 | 80% |
| According | 2 | 50 | | 50 | | | | | | | | | <20 | 40% |
| to | 3 | 90 | | 10 | | | | | | | | | <5 | 80% |
| Present | 4 | 50 | | 10 | | | | 40 | | | | | <10 | 80% |
| Invention | 5 | 70 | | 10 | | | | | 20 | | | | <10 | 80% |
| | 6 | 88 | | 2 | | | | | | 10 | | | <15 | 70% |
| | 7 | 30 | | 20 | | | | | | | 50 | | <20 | 50% |
| | 8 | 60 | | 20 | | | | | | | | 20 | <20 | 50% |
| | 9 | 99.6 | | | 0.4 | | | | | | | | <5 | 90% |
| | 10 | 30 | | | 50 | | | | | 20 | | | <10 | 80% |
| | 11 | 50 | | | 30 | | | | | | | 20 | <20 | 40% |
| | 12 | 60 | | | 20 | | | | | | | 20 | <15 | 50% |
| | 13 | 30 | | | | 70 | | | | | | | <5 | 90% |
| | 14 | 45 | | | | 50 | | | 5 | | | | <15 | 40% |
| | 15 | 50 | | | | 40 | | 10 | | | | | <15 | 60% |
| | 16 | 74.5 | | | | 0.5 | 25 | | | | | | <10 | 80% |
| | 17 | 30 | | | | | 70 | | | | | | <15 | 70% |
| | 18 | 45 | | | | | 40 | | 15 | | | | <10 | 60% |
| | 19 | 60 | | | | | 30 | | | | 10 | | <15 | 60% |
| | 20 | 60 | | | | | 10 | | | | | 30 | <20 | 70% |
| | 21 | 80 | 20 | | | | | | | | | | <40 | 60% |
| | 22 | 90 | 10 | | | | | | | | | | <40 | 60% |
| | 23 | 80 | | 10 | | | 10 | | | | | | <30 | 60% |
| | 24 | 70 | | 30 | | | | | | | | | <30 | 60% |
| | 25 | 70 | | 30 | | | | | | | | | <40 | 60% |

TABLE 1-continued

|  |  | Alloy Powder Mixing Ratio/wt % | | | | | | | | | | Maximum Particle Size in Alloy Powder/μm | Ratio of Powder Component in Paste |
| --- | --- | --- | --- | --- | --- | --- | --- | --- | --- | --- | --- | --- | --- | --- |
|  |  | Ag | Cu | Ti | Zr | Hf | Nb | In | Sn | Mn | Al | Zn | | |
| Comparative Example | 1 | 90 |  | 10 |  |  |  |  |  |  |  |  | <5 | 80% |
|  | 2 | 90 |  | 10 |  |  |  |  |  |  |  |  | <5 | 80% |
|  | 3 | 20 |  | 80 |  |  |  |  |  |  |  |  | <30 | 80% |
|  | 4 | 99.8 |  | 0.2 |  |  |  |  |  |  |  |  | <15 | 80% |
| Conventional Example | 1 | 70.5 | 27 | 2.5 |  |  |  |  |  |  |  |  | <15 | 70% |

TABLE 2

|  |  | Element Powder Mixing Ratio/wt % | | | | | | | | | | | Maximum Particle Size in All Element Powders/μm | Ratio of Powder Component in Paste |
| --- | --- | --- | --- | --- | --- | --- | --- | --- | --- | --- | --- | --- | --- | --- |
|  |  | Ag | Cu | Ti | Zr | Hf | Nb | In | Sn | Mn | Al | Zn | | |
| Example According to Present Invention | 51 | 40 |  | 60 |  |  |  |  |  |  |  |  | <5 | 40% |
|  | 52 | 60 |  | 40 |  |  |  |  |  |  |  |  | <15 | 40% |
|  | 53 | 80 |  | 20 |  |  |  |  |  |  |  |  | <5 | 80% |
|  | 54 | 50 |  | 30 |  |  |  | 20 |  |  |  |  | <5 | 50% |
|  | 55 | 40 |  | 30 |  |  |  |  | 30 |  |  |  | <10 | 40% |
|  | 56 | 94 |  | 1 |  |  |  |  |  | 5 |  |  | <15 | 70% |
|  | 57 | 30 |  | 40 |  |  |  |  |  |  | 30 |  | <10 | 50% |
|  | 58 | 50 |  | 30 |  |  |  |  |  |  |  | 20 | <20 | 60% |
|  | 59 | 50 |  |  | 50 |  |  |  |  |  |  |  | <5 | 70% |
|  | 60 | 40 |  |  | 40 |  |  |  | 20 |  |  |  | <10 | 70% |
|  | 61 | 30 |  |  | 30 |  |  |  |  |  | 40 |  | <20 | 70% |
|  | 62 | 60 |  |  | 20 |  |  |  |  |  |  | 20 | <15 | 90% |
|  | 63 | 30 |  |  |  | 70 |  |  |  |  |  |  | <20 | 40% |
|  | 64 | 50 |  |  |  | 40 |  |  | 10 |  |  |  | <5 | 40% |
|  | 65 | 70 |  |  |  | 20 |  | 10 |  |  |  |  | <20 | 50% |
|  | 66 | 89.5 |  |  |  | 0.5 |  |  |  |  |  | 10 | <10 | 50% |
|  | 67 | 30 |  |  |  |  | 70 |  |  |  |  |  | <10 | 60% |
|  | 68 | 35 |  |  |  |  | 50 | 15 |  |  |  |  | <5 | 40% |
|  | 69 | 45 |  |  |  |  | 5 |  |  | 50 |  |  | <15 | 90% |
|  | 70 | 72 |  |  |  |  | 3 |  |  |  |  | 25 | <20 | 40% |
|  | 71 | 80 |  |  | 20 |  |  |  |  |  |  |  | <30 | 70% |
|  | 72 | 70 |  |  | 30 |  |  |  |  |  |  |  | <30 | 70% |
|  | 73 | 70 |  | 10 |  |  |  |  | 20 |  |  |  | <40 | 80% |
|  | 74 | 70 |  | 20 |  |  |  | 10 |  |  |  |  | <40 | 60% |
|  | 75 | 70 |  | 20 |  |  |  |  | 10 |  |  |  | <40 | 60% |
| Comparative Example | 51 | 80 |  | 20 |  |  |  |  |  |  |  |  | <5 | 80% |
|  | 52 | 59.8 |  |  | 0.2 |  |  | 40 |  |  |  |  | <15 | 70% |
|  | 53 | 10 |  |  |  |  | 80 |  | 10 |  |  |  | <15 | 70% |
| Conventional Example | 51 | 69 | 29 | 2 |  |  |  |  |  |  |  |  | <15 | 70% |

TABLE 3

|  |  | Element Powder Mixing Ratio/wt % | | | | | | | | Content of Active Metal/wt % | | Maximum Particle Size in All Element Powders/μm | Ratio of Powder Component in Paste |
| --- | --- | --- | --- | --- | --- | --- | --- | --- | --- | --- | --- | --- | --- |
|  |  | Ag | TiH$_2$ | ZrH$_2$ | In | Sn | Mn | Al | Zn | Ti | Zr | | |
| Example According to Present Invention | 81 | 65 | 25 |  | 10 |  |  |  |  | 24.0 |  | <15 | 60% |
|  | 82 | 70 | 10 |  |  | 20 |  |  |  | 9.6 |  | <40 | 80% |
|  | 83 | 75 | 15 |  |  |  | 10 |  |  | 14.4 |  | <10 | 70% |
|  | 84 | 80 | 5 |  |  |  |  | 15 |  | 4.8 |  | <30 | 80% |
|  | 85 | 90 | 10 |  |  |  |  |  |  | 9.6 |  | <5 | 80% |
|  | 86 | 80 |  | 10 | 10 |  |  |  |  |  | 9.8 | <40 | 90% |
|  | 87 | 65 |  | 25 |  |  | 10 |  |  |  | 24.6 | <5 | 60% |
|  | 88 | 75 |  | 15 |  |  |  | 10 |  |  | 14.8 | <15 | 80% |
|  | 89 | 75 |  | 20 |  |  |  |  | 5 |  | 19.7 | <30 | 70% |
|  | 90 | 95 |  | 5 |  |  |  |  |  |  | 4.9 | <10 | 60% |
|  | 91 | 60 | 30 |  | 10 |  |  |  |  | 28.8 |  | <15 | 60% |
|  | 92 | 65 | 20 |  |  | 15 |  |  |  | 19.2 |  | <20 | 70% |
|  | 93 | 85 | 10 |  |  |  | 5 |  |  | 9.6 |  | <40 | 80% |
|  | 94 | 70 | 5 |  |  |  |  | 25 |  | 4.8 |  | <5 | 50% |
|  | 95 | 95 | 5 |  |  |  |  |  |  | 4.8 |  | <10 | 50% |

TABLE 3-continued

| | Element Powder Mixing Ratio/wt % | | | | | | | | Content of Active Metal/wt % | | Maximum Particle Size in All Element Powders/μm | Ratio of Powder Component in Paste |
|---|---|---|---|---|---|---|---|---|---|---|---|---|
| | Ag | TiH$_2$ | ZrH$_2$ | In | Sn | Mn | Al | Zn | Ti | Zr | | |
| 96 | 70 | | 10 | 20 | | | | | | 9.8 | <15 | 70% |
| 97 | 65 | | 30 | | 5 | | | | | 29.5 | <30 | 70% |
| 98 | 85 | | 5 | | | 10 | | | | 4.9 | <5 | 60% |
| 99 | 65 | | 20 | | | | | 15 | | 19.7 | <20 | 40% |
| 100 | 80 | | 20 | | | | | | | 19.7 | <10 | 60% |

By bonding ceramic substrates and copper plates to each other using the various pastes shown in Tables 1, 2, and 3, power module substrates which were manufactured using the structure and the manufacturing method of FIG. 10, heat sink-equipped power module substrates which were manufactured using the structure and the manufacturing method of FIGS. 11 and 12, and heat sink-equipped power module substrates which were manufactured using the structure and the manufacturing method of FIGS. 5 and 13 were prepared.

In the power module substrates of FIG. 10, the copper plates were bonded to one surface and the other surface of the ceramic substrate using the above-described various pastes, and a circuit layer and a metal layer were formed of the copper plates. As the copper plates, a rolled sheet of oxygen-free copper was used.

In the heat sink-equipped power module substrates of FIGS. 11 and 12, the copper plate was bonded to one surface of the ceramic substrate using the above-described various pastes to form a circuit layer.

An aluminum plate was bonded to the other surface of the ceramic substrate through a brazing material to form a metal layer. 4N aluminum having a purity of 99.99 mass % was used for the aluminum plate, and a brazing foil consisting of Al-7.5 mass % Si and having a thickness of 20 μm was used as the brazing material.

Further, the aluminum plate formed of A6063 as a heat sink was bonded to the other surface of the metal layer through a brazing material on the metal layer side of the power module substrate. A brazing foil consisting of Al-7.5 mass % Si and having a thickness of 70 μm was used as the brazing material.

In the heat sink-equipped power module substrates of FIGS. 5 and 13, the copper plate was bonded to one surface of the ceramic substrate using the above-described various pastes to form a circuit layer.

An aluminum plate was bonded to the other surface of the ceramic substrate through a brazing material to form a metal layer. 4N aluminum having a purity of 99.99 mass % was used for the aluminum plate, and a brazing foil consisting of Al-7.5 mass % Si and having a thickness of 14 μm was used as the brazing material.

Further, the aluminum plate formed of 4N aluminum as a buffer plate was bonded to the other surface of the metal layer through a brazing material. A brazing foil consisting of Al-7.5 mass % Si and having a thickness of 100 μm was used as the brazing material.

Further, the aluminum plate formed of A6063 as a heat sink was bonded to the other surface of the buffer plate through a brazing material on the metal layer side of the power module substrate. A brazing foil consisting of Al-7.5 mass % Si and having a thickness of 100 μm was used as the brazing material.

The ceramic substrates and the copper plates were bonded to each other under conditions shown in Tables 4, 5, and 6.

During brazing between the ceramic substrate and the aluminum plate, bonding conditions were a vacuum atmosphere, a pressure of 12 kgf/cm$^2$, a heating temperature of 650° C., and a heating time of 30 minutes. Further, during brazing between the aluminum plates, bonding conditions were a vacuum atmosphere, a pressure of 6 kgf/cm$^2$, a heating temperature of 610° C., and a heating time of 30 minutes.

The materials and the sizes of the ceramic substrates are shown in Tables 4, 5, and 6. The sizes of the copper plates were 37 mm×37 mm×0.3 mm. The sizes of the aluminum plates forming the metal layers were 37 mm×37 mm×2.1 mm in the case of the heat sink-equipped power module substrates and were 37 mm×37 mm×0.6 mm in the case of the power module substrates equipped with the heat sink and the buffer plate. The sizes of the aluminum plates forming the heat sinks were 50 mm×60 mm×5 mm. The sizes of the aluminum plates forming the buffer plates were 40 mm×40 mm×0.9 mm.

Tables 4, 5, and 6 show the structures and the manufacturing methods of the power module substrates which were manufactured using the above-described various pastes, the heat sink-equipped power module substrates, and the power module substrates equipped with the heat sink and the buffer plate. Structure "DBC" represents the power module substrate of FIG. 10. Structure "H-1" represents the heat sink-equipped power module substrate of FIG. 11. Structure "H-2" represents the heat sink-equipped power module substrate of FIG. 12. Structure "B-1" represents the heat sink-equipped power module substrate of FIG. 13. Structure "B-2" represents the heat sink-equipped power module substrate of FIG. 5.

TABLE 4

| | | Bonding Conditions | | Ceramic Substrate | | |
|---|---|---|---|---|---|---|
| | | Bonding | | | | |
| | | Temperature/° C. | Load/kgf/cm$^2$ | Material | Size | Structure |
| Example According to | 1 | 820 | 12 | Si$_3$N$_4$ | 40 mm × 40 mm × 0.32 mm | DBC |
| | 2 | 850 | 18 | AlN | 40 mm × 40 mm × 0.635 mm | DBC |
| | 3 | 850 | 18 | Si$_3$N$_4$ | 40 mm × 40 mm × 0.32 mm | H-1 |

TABLE 4-continued

| | | Bonding Conditions | | Ceramic Substrate | | |
|---|---|---|---|---|---|---|
| | | Bonding | | | | |
| | | Temperature/° C. | Load/kgf/cm² | Material | Size | Structure |
| Present Invention | 4 | 820 | 18 | AlN | 40 mm × 40 mm × 0.635 mm | H-2 |
| | 5 | 850 | 18 | Si₃N₄ | 40 mm × 40 mm × 0.32 mm | H-1 |
| | 6 | 790 | 6 | Si₃N₄ | 40 mm × 40 mm × 0.32 mm | B-2 |
| | 7 | 850 | 6 | AlN | 40 mm × 40 mm × 0.635 mm | DBC |
| | 8 | 820 | 6 | Si₃N₄ | 40 mm × 40 mm × 0.32 mm | B-1 |
| | 9 | 850 | 12 | AlN | 40 mm × 40 mm × 0.635 mm | B-1 |
| | 10 | 820 | 18 | Si₃N₄ | 40 mm × 40 mm × 0.32 mm | DBC |
| | 11 | 820 | 12 | Si₃N₄ | 40 mm × 40 mm × 0.32 mm | H-2 |
| | 12 | 790 | 12 | Si₃N₄ | 40 mm × 40 mm × 0.32 mm | DBC |
| | 13 | 790 | 6 | Si₃N₄ | 40 mm × 40 mm × 0.32 mm | B-1 |
| | 14 | 850 | 12 | AlN | 40 mm × 40 mm × 0.635 mm | B-2 |
| | 15 | 790 | 18 | Si₃N₄ | 40 mm × 40 mm × 0.32 mm | B-2 |
| | 16 | 790 | 18 | AlN | 40 mm × 40 mm × 0.635 mm | B-1 |
| | 17 | 820 | 12 | AlN | 40 mm × 40 mm × 0.635 mm | H-2 |
| | 18 | 820 | 18 | AlN | 40 mm × 40 mm × 0.635 mm | H-2 |
| | 19 | 850 | 18 | AlN | 40 mm × 40 mm × 0.635 mm | B-2 |
| | 20 | 790 | 12 | AlN | 40 mm × 40 mm × 0.635 mm | DBC |
| | 21 | 820 | 12 | Si₃N₄ | 40 mm × 40 mm × 0.32 mm | DBC |
| | 22 | 850 | 18 | AlN | 40 mm × 40 mm × 0.635 mm | H-1 |
| | 23 | 850 | 18 | AlN | 40 mm × 40 mm × 0.635 mm | H-1 |
| | 24 | 820 | 6 | AlN | 40 mm × 40 mm × 0.635 mm | H-2 |
| | 25 | 820 | 6 | AlN | 40 mm × 40 mm × 0.635 mm | H-2 |
| Comparative Example | 1 | 790 | 18 | AlN | 40 mm × 40 mm × 0.635 mm | B-1 |
| | 2 | 820 | 6 | AlN | 40 mm × 40 mm × 0.635 mm | B-1 |
| | 3 | 790 | 18 | Si₃N₄ | 40 mm × 40 mm × 0.32 mm | DBC |
| | 4 | 820 | 6 | AlN | 40 mm × 40 mm × 0.635 mm | H-1 |
| Conventional Example | 1 | 850 | 12 | AlN | 40 mm × 40 mm × 0.635 mm | B-1 |

TABLE 5

| | | Bonding Conditions | | Ceramic Substrate | | |
|---|---|---|---|---|---|---|
| | | Bonding | | | | |
| | | Temperature/° C. | Load/kgf/cm² | Material | Size | Structure |
| Example According to Present Invention | 51 | 850 | 12 | AlN | 40 mm × 40 mm × 0.635 mm | DBC |
| | 52 | 820 | 6 | AlN | 40 mm × 40 mm × 0.635 mm | DBC |
| | 53 | 790 | 18 | Si₃N₄ | 40 mm × 40 mm × 0.32 mm | B-2 |
| | 54 | 790 | 6 | Si₃N₄ | 40 mm × 40 mm × 0.32 mm | DBC |
| | 55 | 850 | 3 | AlN | 40 mm × 40 mm × 0.635 mm | DBC |
| | 56 | 820 | 18 | AlN | 40 mm × 40 mm × 0.635 mm | H-1 |
| | 57 | 850 | 6 | AlN | 40 mm × 40 mm × 0.635 mm | B-2 |
| | 58 | 820 | 18 | Si₃N₄ | 40 mm × 40 mm × 0.32 mm | H-1 |
| | 59 | 790 | 12 | Si₃N₄ | 40 mm × 40 mm × 0.32 mm | DBC |
| | 60 | 820 | 6 | AlN | 40 mm × 40 mm × 0.635 mm | H-1 |
| | 61 | 790 | 12 | Si₃N₄ | 40 mm × 40 mm × 0.32 mm | H-2 |
| | 62 | 850 | 18 | AlN | 40 mm × 40 mm × 0.635 mm | B-1 |
| | 63 | 820 | 6 | AlN | 40 mm × 40 mm × 0.635 mm | B-1 |
| | 64 | 850 | 6 | Si₃N₄ | 40 mm × 40 mm × 0.32 mm | B-1 |
| | 65 | 850 | 18 | AlN | 40 mm × 40 mm × 0.635 mm | H-1 |
| | 66 | 820 | 18 | Si₃N₄ | 40 mm × 40 mm × 0.32 mm | DBC |
| | 67 | 790 | 12 | Si₃N₄ | 40 mm × 40 mm × 0.32 mm | B-2 |
| | 68 | 790 | 18 | Si₃N₄ | 40 mm × 40 mm × 0.32 mm | H-1 |
| | 69 | 790 | 12 | Si₃N₄ | 40 mm × 40 mm × 0.32 mm | B-1 |
| | 70 | 850 | 18 | Si₃N₄ | 40 mm × 40 mm × 0.32 mm | H-2 |
| | 71 | 820 | 12 | AlN | 40 mm × 40 mm × 0.635 mm | B-1 |
| | 72 | 850 | 12 | AlN | 40 mm × 40 mm × 0.635 mm | B-1 |
| | 73 | 850 | 12 | AlN | 40 mm × 40 mm × 0.635 mm | B-1 |
| | 74 | 820 | 6 | AlN | 40 mm × 40 mm × 0.635 mm | H-1 |
| | 75 | 820 | 6 | AlN | 40 mm × 40 mm × 0.635 mm | H-1 |
| Comparative Example | 51 | 850 | 12 | AlN | 40 mm × 40 mm × 0.635 mm | H-2 |
| | 52 | 790 | 18 | AlN | 40 mm × 40 mm × 0.635 mm | DBC |
| | 53 | 790 | 18 | AlN | 40 mm × 40 mm × 0.635 mm | H-2 |
| Conventional Example | 51 | 850 | 12 | AlN | 40 mm × 40 mm × 0.635 mm | B-1 |

TABLE 6

| | | Bonding Conditions | | | |
|---|---|---|---|---|---|
| | | Bonding | | Ceramic Substrate | |
| | | Temperature/° C. | Load/kgf/cm² | Material | Size | Structure |
| Example | 81 | 850 | 6 | AlN | 40 mm × 40 mm × 0.635 mm | DBC |
| According | 82 | 820 | 3 | AlN | 40 mm × 40 mm × 0.635 mm | DBC |
| to | 83 | 790 | 6 | AlN | 40 mm × 40 mm × 0.635 mm | DBC |
| Present | 84 | 790 | 18 | AlN | 40 mm × 40 mm × 0.635 mm | DBC |
| Invention | 85 | 850 | 12 | AlN | 40 mm × 40 mm × 0.635 mm | DBC |
| | 86 | 790 | 12 | AlN | 40 mm × 40 mm × 0.635 mm | DBC |
| | 87 | 820 | 6 | AlN | 40 mm × 40 mm × 0.635 mm | DBC |
| | 88 | 790 | 6 | AlN | 40 mm × 40 mm × 0.635 mm | DBC |
| | 89 | 850 | 3 | AlN | 40 mm × 40 mm × 0.635 mm | DBC |
| | 90 | 820 | 12 | AlN | 40 mm × 40 mm × 0.635 mm | DBC |
| | 91 | 790 | 12 | AlN | 40 mm × 40 mm × 0.635 mm | DBC |
| | 92 | 820 | 6 | AlN | 40 mm × 40 mm × 0.635 mm | DBC |
| | 93 | 850 | 18 | AlN | 40 mm × 40 mm × 0.635 mm | DBC |
| | 94 | 790 | 6 | AlN | 40 mm × 40 mm × 0.635 mm | DBC |
| | 95 | 820 | 3 | AlN | 40 mm × 40 mm × 0.635 mm | DBC |
| | 96 | 790 | 18 | AlN | 40 mm × 40 mm × 0.635 mm | DBC |
| | 97 | 850 | 6 | AlN | 40 mm × 40 mm × 0.635 mm | DBC |
| | 98 | 820 | 18 | AlN | 40 mm × 40 mm × 0.635 mm | DBC |
| | 99 | 790 | 12 | AlN | 40 mm × 40 mm × 0.635 mm | DBC |
| | 100 | 850 | 6 | AlN | 40 mm × 40 mm × 0.635 mm | DBC |

The equivalent thicknesses (average equivalent thicknesses) were measured as follows, and the measurement results are shown in Tables 7, 8, and 9.

First, the various pastes shown in Tables 1, 2, and 3 were coated on surfaces of the ceramic substrates and the copper plates, followed by drying. The equivalent thicknesses (average equivalent thicknesses) of the respective elements of the dried various pastes were measured.

Figure 14:
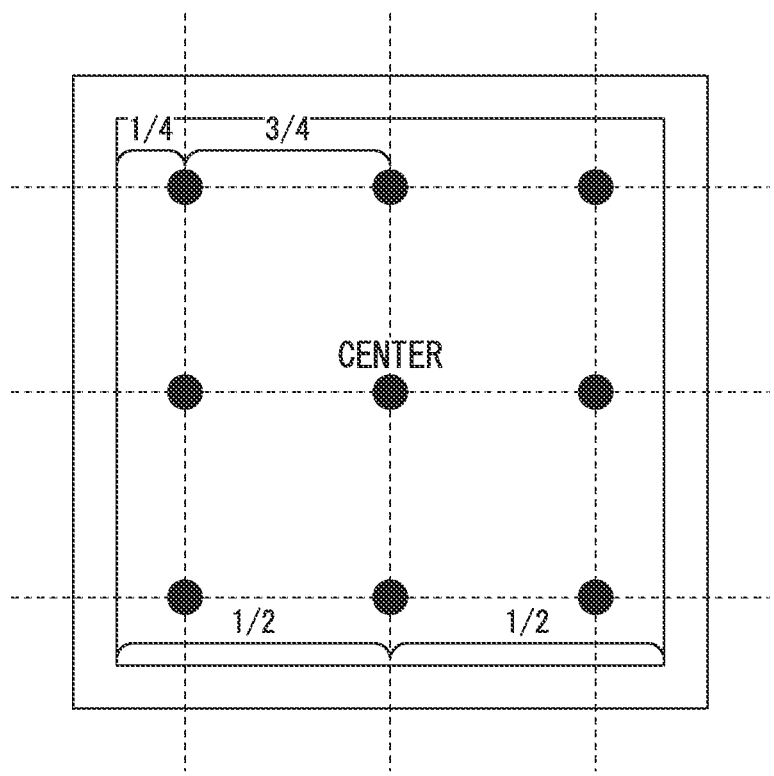
FIG. 14 is a plan view illustrating positions where the thickness is measured in Examples.

The thicknesses of the coated various pastes were measured three times using an X-ray fluorescent analysis thickness meter (trade name "STF 9400" manufactured by SII Nanotechnology Inc.) at positions (9 positions) shown in FIG. 14, and the average value thereof was obtained. The thicknesses of known samples were measured in advance to obtain a relationship between a fluorescent X-ray intensity and a density. Based on the results, the equivalent thicknesses of the respective elements were determined from the fluorescent X-ray intensities measured in the respective samples.

TABLE 7

| | | Average Equivalent Thickness/μm | | | | | | | | | | |
|---|---|---|---|---|---|---|---|---|---|---|---|---|
| | | Ag | Cu | Ti | Zr | Hf | Nb | In | Sn | Mn | Al | Zn | Total |
| Example | 1 | 1.70 | | 4.85 | | | | | | | | | 6.55 |
| According | 2 | 5.12 | | 4.87 | | | | | | | | | 9.99 |
| to | 3 | 9.94 | | 1.05 | | | | | | | | | 10.99 |
| Present | 4 | 2.65 | | 0.51 | | 6.00 | | | | | | | 9.16 |
| Invention | 5 | 5.69 | | 0.77 | | | 4.79 | | | | | | 11.25 |
| | 6 | 4.94 | | 0.11 | | | | | | 2.69 | | | 7.74 |
| | 7 | 1.19 | | 0.76 | | | | | | | 9.17 | | 11.12 |
| | 8 | 2.12 | | 0.67 | | | | | | | | 5.75 | 8.54 |
| | 9 | 9.43 | | | 0.04 | | | | | | | | 9.47 |
| | 10 | 1.56 | | | 2.48 | | | | | 2.83 | | | 6.87 |
| | 11 | 1.23 | | | 0.70 | | | | | | | 6.14 | 8.07 |
| | 12 | 2.14 | | | 0.68 | | | | | | | 6.42 | 9.24 |
| | 13 | 1.55 | | | | 3.44 | | | | | | | 4.99 |
| | 14 | 1.13 | | | | 1.20 | | | 2.13 | | | | 4.46 |
| | 15 | 1.32 | | | | 1.00 | | 2.03 | | | | | 4.35 |
| | 16 | 4.45 | | | | 0.04 | 3.55 | | | | | | 8.04 |
| | 17 | 1.11 | | | | | 2.47 | | | | | | 3.58 |
| | 18 | 1.73 | | | | | 1.47 | | 3.81 | | | | 7.01 |
| | 19 | 2.25 | | | | | 1.07 | | | | 2.16 | | 5.48 |
| | 20 | 1.41 | | | | | 0.22 | | | | 3.13 | | 4.76 |
| | 21 | 13.51 | | 3.22 | | | | | | | | | 16.73 |
| | 22 | 14.32 | | 1.52 | | | | | | | | | 15.84 |
| | 23 | 14.50 | | 2.50 | | | | 0.58 | | | | | 17.58 |
| | 24 | 15.07 | | 6.15 | | | | | | | | | 21.22 |
| | 25 | 13.99 | | 5.71 | | | | | | | | | 19.70 |
| Comparative | 1 | 18.79 | | 0.85 | | | | | | | | | 19.64 |
| Example | 2 | 27.14 | | 1.23 | | | | | | | | | 28.37 |
| | 3 | 22.31 | | 85.05 | | | | | | | | | 107.36 |
| | 4 | 5.98 | | 0.01 | | | | | | | | | 5.99 |
| Conventional Example | 1 | 16.57 | 6.05 | 0.56 | | | | | | | | | 23.18 |

TABLE 8

| | | Average Equivalent Thickness/μm | | | | | | | | | | |
|---|---|---|---|---|---|---|---|---|---|---|---|---|
| | | Ag | Cu | Ti | Zr | Hf | Nb | In | Sn | Mn | Al | Zn | Total |
| Example According to Present Invention | 51 | 3.35 | | 4.78 | | | | | | | | | 8.13 |
| | 52 | 6.91 | | 4.39 | | | | | | | | | 11.30 |
| | 53 | 8.55 | | 2.04 | | | | | | | | | 10.59 |
| | 54 | 2.19 | | 1.25 | | | | 6.62 | | | | | 10.06 |
| | 55 | 1.97 | | 1.40 | | | | | 7.76 | | | | 11.13 |
| | 56 | 10.61 | | 0.11 | | | | | | 2.77 | | | 13.49 |
| | 57 | 1.46 | | 1.86 | | | | | | | 7.46 | | 10.78 |
| | 58 | 1.23 | | 0.70 | | | | | | | | 2.63 | 4.56 |
| | 59 | 4.50 | | | 4.29 | | | | | | | | 8.79 |
| | 60 | 3.02 | | | 2.87 | | | 0.48 | | | | | 6.37 |
| | 61 | 1.84 | | | 1.75 | | | | | | 6.80 | | 10.39 |
| | 62 | 2.18 | | | 0.69 | | | | | | 1.16 | | 4.03 |
| | 63 | 1.33 | | | | 2.95 | | | | | | | 4.28 |
| | 64 | 1.25 | | | | 0.96 | | | 4.07 | | | | 6.28 |
| | 65 | 1.27 | | | | 0.35 | | 1.93 | | | | | 3.55 |
| | 66 | 4.86 | | | | 0.03 | | | | | | 5.50 | 10.39 |
| | 67 | 1.54 | | | | | 3.43 | | | | | | 4.97 |
| | 68 | 1.30 | | | | | 1.77 | | 7.54 | | | | 10.61 |
| | 69 | 1.96 | | | | | 0.21 | | | 3.93 | | | 6.10 |
| | 70 | 1.34 | | | | | 0.05 | | | | 6.46 | | 7.85 |
| | 71 | 15.18 | | | 3.62 | | | | | | | | 18.80 |
| | 72 | 13.94 | | | 5.69 | | | | | | | | 19.63 |
| | 73 | 14.78 | | 2.91 | | | | | 1.34 | | | | 19.03 |
| | 74 | 14.92 | | 4.06 | | | | 0.68 | | | | | 19.66 |
| | 75 | 14.93 | | 4.06 | | | | | 0.68 | | | | 19.67 |
| Comparative Example | 51 | 23.34 | | 2.39 | | | | | | | | | 25.73 |
| | 52 | 6.88 | | | 0.02 | | | | 4.39 | | | | 11.29 |
| | 53 | 1.14 | | | | | 8.72 | | | | 1.10 | | 10.96 |
| Conventional Example | 51 | 16.23 | 6.50 | 0.45 | | | | | | | | | 23.18 |

TABLE 9

| | | Average Equivalent Thickness/μm | | | | | | | | |
|---|---|---|---|---|---|---|---|---|---|---|
| | | Ag | Ti | Zr | In | Sn | Mn | Al | Zn | Total |
| Example According to Present Invention | 81 | 1.55 | 0.51 | | 0.26 | | | | | 2.32 |
| | 82 | 6.20 | 0.85 | | | 1.77 | | | | 8.82 |
| | 83 | 8.98 | 1.69 | | | | 1.18 | | | 11.85 |
| | 84 | 6.81 | 0.43 | | | | | 1.27 | | 8.51 |
| | 85 | 8.25 | 0.87 | | | | | | | 9.12 |
| | 86 | 7.25 | | 0.88 | | 0.89 | | | | 9.02 |
| | 87 | 2.21 | | 0.83 | | | 0.35 | | | 3.39 |
| | 88 | 10.22 | | 2.01 | | | | 1.26 | | 13.49 |
| | 89 | 2.76 | | 0.71 | | | | | 0.18 | 3.65 |
| | 90 | 8.25 | | 0.44 | | | | | | 8.69 |
| | 91 | 1.94 | 0.94 | | 0.33 | | | | | 3.21 |
| | 92 | 3.76 | 1.09 | | | 0.87 | | | | 5.72 |
| | 93 | 14.77 | 1.65 | | | | 0.86 | | | 17.28 |
| | 94 | 1.62 | 0.13 | | | | | 0.62 | | 2.37 |
| | 95 | 4.73 | 0.26 | | | | | | | 4.99 |
| | 96 | 3.63 | | 0.55 | 1.13 | | | | | 5.31 |
| | 97 | 3.89 | | 1.72 | | 0.30 | | | | 5.91 |
| | 98 | 5.65 | | 0.31 | | | 0.65 | | | 6.61 |
| | 99 | 2.40 | | 0.72 | | | | | 0.58 | 3.70 |
| | 100 | 3.10 | | 0.74 | | | | | | 3.84 |

Regarding the power module substrates and the heat sink-equipped power module substrates obtained as above, the ceramic cracking, the bonding ratio after the application of a cooling-heating cycle, whether or not there is a nitride layer, and the thickness of an Ag—Cu eutectic structure layer were evaluated. The evaluation results are shown in Tables 10, 11, and 12.

Whether or not there were cracks was determined for each cooling-heating cycle (−45° C.↔125° C.) which was repeated 5000 times. Based on the number of cooling-heating cycles where cracks were confirmed, the ceramic cracking was evaluated.

The bonding ratio after the application of a cooling-heating cycle was calculated according to the following expression using the power module substrates after repeating the cooling-heating cycle (−45° C.↔125° C.) 4000 times. When cracks were formed before 3500 cycles, the bonding ratio after 4000 cycles was not evaluated.

Bonding Ratio=(Initial Bonding Area−Peeled Area)/Initial Bonding Area

In order to determine whether or not there was a nitride layer, whether or not there is a nitride-forming element at an interface between the copper plate and the ceramic substrate was determined based on mapping of the nitride-forming element obtained by EPMA (electron probe microanalyzer).

In order to obtain the thickness of the Ag—Cu eutectic structure layer, based on a backscattered electron image of an interface between the copper plate and the ceramic substrate which was obtained using an EPMA (electron probe microanalyzer), the area of the Ag—Cu eutectic structure layer which was continuously formed on the bonding interface was measured in a visual field (length: 45 μm, width: 60 μm) at a magnification of 2000 times and was divided by the width of the measurement visual field. The average of the thicknesses in five visual fields was obtained as the thickness of the Ag—Cu eutectic structure layer. In the Ag—Cu eutectic structure layer formed in the bonding portion between the copper plate and the ceramic substrate, regions which were not continuously formed on the bonding interface in the thickness direction were excluded during the measurement of the area of the Ag—Cu eutectic structure layer.

TABLE 10

| | | Nitride Layer | Thickness of Eutectic Structure Layer/μm | Ceramic Cracking | Bonding Ratio (After 4000 Cycles) |
|---|---|---|---|---|---|
| Example According to Present Invention | 1 | Present | <1 | >4000 | 98.2% |
| | 2 | Present | 4 | >4000 | 98.7% |
| | 3 | Present | 8 | 3500-4000 | 93.8% |
| | 4 | Present | 2 | >4000 | 96.9% |
| | 5 | Present | 5 | >4000 | 99.0% |
| | 6 | Present | 5 | >4000 | 96.9% |
| | 7 | Present | <1 | >4000 | 100.0% |
| | 8 | Present | 2 | >4000 | 97.5% |
| | 9 | Present | 8 | 3500-4000 | 98.3% |
| | 10 | Present | <1 | >4000 | 94.8% |
| | 11 | Present | <1 | >4000 | 97.3% |
| | 12 | Present | 2 | >4000 | 94.7% |
| | 13 | Present | <1 | >4000 | 94.8% |
| | 14 | Present | <1 | >4000 | 96.4% |
| | 15 | Present | <1 | >4000 | 96.0% |
| | 16 | Present | 4 | >4000 | 99.7% |
| | 17 | Present | <1 | >4000 | 94.1% |
| | 18 | Present | <1 | >4000 | 96.3% |
| | 19 | Present | 2 | >4000 | 96.9% |
| | 20 | Present | <1 | >4000 | 95.7% |
| | 21 | Present | 13 | >4000 | 92.8% |
| | 22 | Present | 14 | >4000 | 94.1% |
| | 23 | Present | 14 | 3500-4000 | 91.8% |
| | 24 | Present | 15 | 3500-4000 | 94.6% |
| | 25 | Present | 14 | 3500-4000 | 93.5% |
| Comparative Example | 1 | Present | 19 | 1500-2000 | Stopped at 2000 Cycles |
| | 2 | Present | 27 | 0-500 | Stopped at 500 Cycles |
| | 3 | Present | 22 | 500-1000 | Stopped at 1000 Cycles |
| | 4 | None | 6 | >4000 | 69.70% |
| Conventional Example | 1 | Present | 22 | 1500-2000 | Stopped at 2000 Cycles |

TABLE 11

| | | Nitride Layer | Thickness of Eutectic Structure Layer/μm | Number of Cycles where Cracks Were Formed/Cycles | Bonding Ratio (After 4000 Cycles) |
|---|---|---|---|---|---|
| Example According to Present Invention | 51 | Present | 3 | >4000 | 98.7% |
| | 52 | Present | 7 | 3500-4000 | 97.5% |
| | 53 | Present | 8 | 3500-4000 | 96.3% |
| | 54 | Present | 2 | >4000 | 96.7% |
| | 55 | Present | 2 | >4000 | 98.2% |
| | 56 | Present | 9 | 3500-4000 | 93.9% |

TABLE 11-continued

| | | Nitride Layer | Thickness of Eutectic Structure Layer/μm | Number of Cycles where Cracks Were Formed/Cycles | Bonding Ratio (After 4000 Cycles) |
|---|---|---|---|---|---|
| | 57 | Present | <1 | >4000 | 98.5% |
| | 58 | Present | <1 | >4000 | 97.1% |
| | 59 | Present | 4 | >4000 | 95.3% |
| | 60 | Present | 3 | >4000 | 94.0% |
| | 61 | Present | 2 | >4000 | 94.7% |
| | 62 | Present | 2 | >4000 | 96.4% |
| | 63 | Present | <1 | >4000 | 99.0% |
| | 64 | Present | <1 | >4000 | 93.1% |
| | 65 | Present | <1 | >4000 | 96.1% |
| | 66 | Present | 4 | >4000 | 97.3% |
| | 67 | Present | <1 | >4000 | 99.1% |
| | 68 | Present | <1 | 3500-4000 | 95.5% |
| | 69 | Present | 2 | >4000 | 96.5% |
| | 70 | Present | <1 | >4000 | 95.3% |
| | 71 | Present | 15 | 3500-4000 | 93.8% |
| | 72 | Present | 14 | >4000 | 94.5% |
| | 73 | Present | 15 | 3500-4000 | 91.3% |
| | 74 | Present | 15 | 3500-4000 | 92.7% |
| | 75 | Present | 15 | >4000 | 93.4% |
| Comparative Example | 51 | Present | 23 | 1500-2000 | Stopped at 2000 Cycles |
| | 52 | None | 7 | 3500-4000 | 64.8% |
| | 53 | Present | <1 | 1500-2000 | Stopped at 2000 Cycles |
| Conventional Example | 51 | Present | 22 | 1500-2000 | Stopped at 2000 Cycles |

TABLE 12

| | | Nitride Layer | Thickness of Eutectic Structure Layer/μm | Number of Cycles where Cracks Were Formed/Cycles | Bonding Ratio (After 4000 Cycles) |
|---|---|---|---|---|---|
| Example According to Present Invention | 81 | Present | <1 | >4000 | 99.5% |
| | 82 | Present | 6 | >4000 | 99.3% |
| | 83 | Present | 9 | 3500-4000 | 98.1% |
| | 84 | Present | 6 | >4000 | 97.4% |
| | 85 | Present | 8 | >4000 | 98.7% |
| | 86 | Present | 7 | >4000 | 99.1% |
| | 87 | Present | 2 | >4000 | 98.6% |
| | 88 | Present | 9 | 3500-4000 | 98.4% |
| | 89 | Present | 3 | >4000 | 98.8% |
| | 90 | Present | 8 | >4000 | 98.3% |
| | 91 | Present | 2 | >4000 | 99.1% |
| | 92 | Present | 4 | >4000 | 98.5% |
| | 93 | Present | 14 | 3500-4000 | 97.2% |
| | 94 | Present | 3 | >4000 | 95.8% |
| | 95 | Present | 4 | >4000 | 99.4% |
| | 96 | Present | 3 | >4000 | 98.3% |
| | 97 | Present | 3 | >4000 | 98.4% |
| | 98 | Present | 5 | >4000 | 97.4% |
| | 99 | Present | 2 | >4000 | 96.3% |
| | 100 | Present | 3 | >4000 | 99.3% |

In Comparative Examples 1 to 3 and 51, the thickness of the eutectic structure layer was greater than 15 μm, and cracks were formed on the ceramic substrate at a small number of cycles.

In Conventional Examples 1 and 51, the thickness of the eutectic structure layer was greater than 15 μm, and cracks were formed on the ceramic substrate at a small number of cycles similarly to the case of the comparative examples.

On the other hand, in Examples 1 to 25, 51 to 75, and 81 to 100 according to the present invention in which the thickness of the eutectic structure layer was 15 μm or less, it was confirmed that the cracking of the ceramic substrate was suppressed. The bonding ratio after 4000 cycles was high at 91% or higher.

It was confirmed from the above results that, according to the examples according to the present invention, a power module substrate capable of suppressing cracking of a ceramic substrate during the application of a cooling-heating cycle can be provided.

In Comparative Examples 3 and 53 in which the content of the nitride-forming element was 75 mass % or greater, the content of Ag was small. Therefore, a molten metal region was not sufficiently formed at the interface between the copper plate and the ceramic substrate, and cracks were formed before 4000 cycles. In Comparative Examples 4 and 52 in which the content of the nitride-forming element was less than 0.4 mass %, a nitride layer was not sufficiently formed, and the bonding ratio after 4000 cycles was poor at 70% or lower.

On the other hand, in Examples 1 to 25, 51 to 75, and 81 to 100 according to the present invention in which the content of the nitride-forming element was 0.4 mass % to less than 75 mass %, it was confirmed that the cracking of the ceramic substrate was suppressed. The bonding ratio after 4000 cycles was high at 91% or higher. It was confirmed from the above results that, according to the examples according to the present invention, even when a copper member and a ceramic member are bonded to each other, the copper member-bonding paste capable of suppressing the cracking of the ceramic member and reliably bonding the copper member and the ceramic member to each other can be provided.

INDUSTRIAL APPLICABILITY

According to the present invention, in a power module substrate in which a copper plate formed of copper or a copper alloy is bonded to a ceramic substrate, the cracking of the ceramic substrate can be suppressed during the application of a cooling-heating cycle. Therefore, the present invention has high industrial applicability.

REFERENCE SIGNS LIST

1 POWER MODULE
3 SEMICONDUCTOR ELEMENT (ELECTRONIC COMPONENT)
10, 110, 210, 310, 410 POWER MODULE SUBSTRATE
11, 111, 211, 311, 411 CERAMIC SUBSTRATE
12, 112, 212, 312, 412 CIRCUIT LAYER
13, 113, 213, 313, 413 METAL LAYER
22, 122, 123, 222, 322, 422 COPPER PLATE
23, 223, 323, 423 ALUMINUM PLATE
31, 131 NITRIDE LAYER
32 Ag—Cu EUTECTIC STRUCTURE LAYER
41, 441 BUFFER PLATE
50, 250, 350, 450 POWER MODULE SUBSTRATE WITH A HEAT SINK
51, 251, 351, 451 HEAT SINK

The invention claimed is:

1. A method of manufacturing a power module substrate including a copper plate that is formed of copper or a copper alloy and is laminated and bonded on a surface of a ceramic substrate, the method comprising:
  a copper member-bonding paste coating process of coating a copper member-bonding paste and forming an Ag-nitride-forming element layer, which contains Ag and a nitride-forming element, on at least one of a bonding surface of the ceramic substrate and a bonding surface of the copper plate;
  a laminating process of laminating the ceramic substrate and the copper plate through the Ag-nitride-forming element layer;
  a heating process of pressing and heating a laminate of the ceramic substrate and the copper plate in a laminating direction to form a molten metal region at an interface between the ceramic substrate and the copper plate; and
  a solidification process of solidifying the molten metal region to bond the ceramic substrate and the copper plate to each other,
  wherein the copper member-bonding paste includes a powder component containing Ag and the nitride-forming element, a resin, and a solvent, and the powder component contains 0.4 mass % to 75 mass % of the nitride-forming element and a balance consisting of Ag and unavoidable impurities,
  the copper member-bonding paste coating process is configured to form Ag-nitride-forming element layer including the nitride-forming element having an average equivalent thickness of 0.03 μm to 6.15 μm or less when measured by an X-ray fluorescent analysis thickness meter, and
  in the heating process, the copper plate and the ceramic substrate are heated while being pressed by a pressure of 1 kgf/cm$^2$ to 35 kgf/cm$^2$ in a laminating direction thereof, and Ag is diffused to the copper plate side to form the molten metal region at the interface between the ceramic substrate and the copper plate and to form a nitride layer on a surface of the ceramic substrate.

2. The method of manufacturing a power module substrate according to claim 1, wherein the nitride-forming element is at least one of elements selected from Ti, Hf, Zr, and Nb.

3. The method of manufacturing a power module substrate according to claim 1, wherein in the copper member-bonding paste coating process, at least one of additional elements selected from In, Sn, Al, Mn, and Zn are added in addition to Ag and the nitride-forming element.

4. The method of manufacturing a power module substrate according to claim 1, wherein the ceramic substrate is formed of AlN or $Si_3N_4$.

5. The method of manufacturing a power module substrate according to claim 1, wherein the Ag-nitride-forming element layer-containing paste contains a hydride of the nitride-forming element.

6. The method of manufacturing a power module substrate according to claim 1, wherein a particle size of powder forming the powder component is 40 μm or less.

7. The method of manufacturing a power module substrate according to claim 1, wherein the content of the powder component in the copper member-bonding paste is 40 mass % to 90 mass %.

8. The method of manufacturing a power module substrate according to claim 1, wherein the copper member-bonding paste further contains at least one of a dispersant, a plasticizer, and a reducing agent.

* * * * *